United States Patent
Wang et al.

(10) Patent No.: US 12,378,168 B2
(45) Date of Patent: Aug. 5, 2025

(54) METHODS FOR REDUCING FORMATION OF CARBON DISULFIDE IN STEAM CRACKING PROCESSES TO PRODUCE OLEFINS

(71) Applicant: Dow Global Technologies LLC, Midland, MI (US)

(72) Inventors: Hangyao Wang, Pearland, TX (US); Jorge H. Pazmino, Pearland, TX (US); Yu Liu, Lake Jackson, TX (US); Georgios Bellos, Terneuzen (NL)

(73) Assignee: Dow Global Technologies LLC, Midland, MI (US)

( * ) Notice: Subject to any disclaimer, the term of this patent is extended or adjusted under 35 U.S.C. 154(b) by 225 days.

(21) Appl. No.: 18/001,811

(22) PCT Filed: Jun. 17, 2021

(86) PCT No.: PCT/US2021/037732
§ 371 (c)(1),
(2) Date: Dec. 14, 2022

(87) PCT Pub. No.: WO2022/005755
PCT Pub. Date: Jan. 6, 2022

(65) Prior Publication Data
US 2023/0227382 A1 Jul. 20, 2023

(30) Foreign Application Priority Data
Jun. 29, 2020 (EP) .................................... 20386034

(51) Int. Cl.
*C07C 4/04* (2006.01)
*C07C 5/09* (2006.01)
(Continued)

(52) U.S. Cl.
CPC .................. *C07C 4/04* (2013.01); *C07C 5/09* (2013.01); *C07C 7/14858* (2013.01);
(Continued)

(58) Field of Classification Search
None
See application file for complete search history.

(56) References Cited

U.S. PATENT DOCUMENTS 5,463,159 A  10/1995 Callejas et al.
6,514,631 B1 * 2/2003 Yamamoto .......... C22C 33/0228
                                              428/685
(Continued)

FOREIGN PATENT DOCUMENTS

CN  110997601 A  4/2020
NL  2024522 A  1/2020

OTHER PUBLICATIONS

International Search Report and Written Opinion issued by the European Patent Office acting as International Searching Authority for International Patent Application No. PCT/US2021/037732 dated Jul. 23, 2021 (13 total pages).
(Continued)

*Primary Examiner* — Ali Z Fadhel
(74) *Attorney, Agent, or Firm* — Dinsmore & Shohl LLP

(57) ABSTRACT

Methods for producing olefins through hydrocarbon steam cracking include passing a hydrocarbon feed that includes one or more hydrocarbons to a hydrocarbon cracking unit and passing one or more sulfur-containing compounds to the hydrocarbon cracking unit. The sulfur-containing compounds include at least hydrogen sulfide gas, and a flow rate of the sulfur-containing compounds to the hydrocarbon cracking unit is sufficient to produce a molar concentration of elemental sulfur in the hydrocarbon cracking unit of from 10 ppm to 200 ppm. The methods include cracking the
(Continued)

hydrocarbon feed in the hydrocarbon cracking unit to produce a cracker effluent and contacting the cracker effluent with a quench fluid in a quench unit to produce at least a cracked gas and a first pygas. The first pygas has a concentration of carbon disulfide less than 50 ppmw based on the total mass flow rate of the first pygas.

14 Claims, 6 Drawing Sheets

(51) Int. Cl.
  *C07C 7/148* (2006.01)
  *C10G 9/36* (2006.01)
  *C10G 69/06* (2006.01)
  *C10G 75/02* (2006.01)
(52) U.S. Cl.
  CPC ............ *C07C 7/14875* (2013.01); *C10G 9/36* (2013.01); *C10G 69/06* (2013.01); *C10G 75/02* (2013.01); *C10G 2300/202* (2013.01); *C10G 2300/207* (2013.01); *C10G 2300/4075* (2013.01); *C10G 2400/02* (2013.01)

(56) References Cited

U.S. PATENT DOCUMENTS

| | | |
|---|---|---|
| 6,673,232 B2 | 1/2004 | Lindstrom |
| 2012/0203039 A1 | 8/2012 | Smith, Jr. |
| 2020/0318016 A1* | 10/2020 | Jamieson ................ C08F 10/06 |

OTHER PUBLICATIONS

Ziarifar E., et al., "Using disulfide oil as coke inhibitor to reduce environmental hazards in olefin heaters", Advances in Environmental Technology, vol. 3 (2018) pp. 183-186.
Edgar L. Mohundro, "Overview on C2 and C3 Selective Hydrogenation in Ethylene Plants", 15th Ethylene Produces Conference, 2003 AICHE, 30 total pages.
Saudi Arabian Second Examination Report dated Mar. 11, 2024, pertaining to SA Patent Application No. 522441728, 3 pgs.
Saudi Arabian Examination Report, dated Aug. 17, 2023, pertaining to Saudi Abrabian Patent Application No. 522441728, 14 pgs.
Chinese Office Action dated Mar. 6, 2025, pertaining to CN Patent Application No. 202180042985.2, 16 pgs.

* cited by examiner

METHODS FOR REDUCING FORMATION OF CARBON DISULFIDE IN STEAM CRACKING PROCESSES TO PRODUCE OLEFINS

CROSS-REFERENCE TO RELATED APPLICATIONS

This application is a National Stage Entry under 35 U.S.C. § 371 of International Patent Application No. PCT/2021/037732, filed Jun. 17, 2021, which claims the benefit of priority to European Patent Application No. 20386034.1, filed on Jun. 29, 2020 and entitled "Methods for Reducing Formation of Carbon Disulfide in Steam Cracking Processes to Produce Olefins," the entire contents of both of which are incorporated by reference herein.

BACKGROUND

Field

The present disclosure generally relates to chemical processing systems and methods for producing olefins and the operation thereof and, more specifically, to methods for reducing formation of carbon disulfide in steam cracking systems for producing olefins.

Technical Background

Light olefins may be utilized as base materials to produce many types of goods and materials. For example, ethylene may be utilized to manufacture polyethylene, ethylene chloride, or ethylene oxides. Such products may be utilized in product packaging, construction, textiles, etc. Thus, there is an industry demand for light olefins, such as ethylene, propylene, and butene.

Light olefins may be produced by different reaction processes depending on the given chemical feed stream, such as a product stream from a petrochemical operation. For example, hydrocarbon cracking (e.g., steam cracking) may be used to produce olefins from a hydrocarbon stream. However, hydrocarbon cracking and other processes for producing light olefins can produce byproducts and impurities, such as acetylenic and allenic compounds, which can be poisons to downstream processes and catalysts and may present a safety concerns in downstream processes due to the reactivity of these compounds. Acetylene and other impurities and byproducts can be removed from an olefin-containing hydrocarbon cracking effluent through selective hydrogenation. Coke may also be produced in the hydrocarbon cracking process and can deposit and buildup on internal furnace coils within the hydrocarbon cracking unit.

SUMMARY

In conventional steam cracking units for converting hydrocarbons to olefins, sulfur in the form of organosulfur compounds, such as dimethyl disulfide (DMDS), dimethyl sulfide (DMS), diethyl disulfide (DEDS), diethyl sulfide (DES), methyl mercaptan (MM), or combinations thereof, are often introduced to the steam cracking unit to passivate the internal coil surface to reduce coke formation on the internal furnace coils, which can increase the lifetime of the coils. The organosulfur compounds can also be added to decrease or control the amount of carbon monoxide (CO) generated in the steam cracking unit to meet the desired concentration of CO in the acetylene hydrogenation reactors downstream of the steam cracking unit. DMDS and other organosulfur compounds are often employed to reduce coke in steam cracking units because they are liquids at ambient temperatures and are easily handled to be introduced to the hydrocarbon cracking unit.

However, organosulfur compounds, such as DMDS, undergo decomposition under the reaction conditions in the hydrocarbon cracking unit. The decomposition of these organosulfur compounds at the reaction conditions in the hydrocarbon cracking unit produces sulfur impurities, such as but not limited to carbon disulfide and methyl mercaptan. The carbon disulfide and other organosulfur impurities may be present in pygas streams separated from the cracked gas, before or after the acetylene hydrogenation unit. As further discussed herein, carbon disulfide may exit the system in a first pygas produced by a quench unit downstream of the hydrocarbon cracking unit and/or in a second pygas or third pygas from one or more separation units downstream of the quench unit. When the cracked gas is separated in a cracked gas separation unit upstream of the acetylene hydrogenation unit into a hydrogenation feed and a cracked gas bottom stream, the cracked gas bottom stream may be further separated to produce the second pygas. When the cracked gas is passed directly to the acetylene hydrogenation unit without separation, a third pygas may be recovered from the hydrogenation effluent as a bottom stream from a hydrogenation effluent separation system. Methyl mercaptan may pass out of the system in a C4 stream from the hydrogenation effluent separation system downstream of the acetylene hydrogenation unit.

The amount of carbon disulfide, methyl mercaptan, or both, produced in the steam cracking unit may cause one or more product streams, such as the first pygas, second pygas, third pygas, or combinations of these, to be out-of-specification. Additionally, the presence of carbon disulfide, methyl mercaptan, or both, in the product streams may also cause problems in downstream processes and applications.

Therefore, there is an ongoing need to reduce coke buildup and control CO formation in hydrocarbon cracking units while at the same time reducing the formation of sulfur containing impurities. The present disclosure is directed to systems and processes for producing olefins, where the systems and processes include thermally cracking of a hydrocarbon feed in a hydrocarbon cracking unit to produce a cracker effluent, quenching the cracker effluent to produce a first pygas and a cracked gas. The cracked gas may be separated into a hydrogenation feed and a cracked gas bottom stream, and the hydrogenation feed may be hydrogenated in an acetylene hydrogenation unit to produce a hydrogenation effluent comprising one or more olefin products. The cracked gas bottoms stream may be further separated in a cracked gas bottoms separation unit to produce a second pygas. Alternatively, the cracked gas may be passed directly to the acetylene hydrogenation unit without separation and hydrogenated to produce the hydrogenation effluent, and the hydrogenation effluent may then be further separated in a hydrogenation effluent separation system to produce a third pygas and one or more product streams comprising olefins.

The systems and processes disclosed herein may include passing hydrogen sulfide ($H_2S$) to the hydrocarbon cracking unit. The $H_2S$ may replace all or at least a portion of the organosulfur compounds introduced to the steam cracking unit. The $H_2S$ gas may be diluted in a light hydrocarbon, such as ethane, propane, or a combination of these. The introduction of $H_2S$ gas to the steam cracking unit may reduce or eliminate the amount of organosulfur compounds, such as but not limited to DMDS, DMS, DEDS, DES, MM, or combinations thereof, introduced to the hydrocarbon cracking unit. The introduction of $H_2S$ to replace or eliminate organosulfur compounds introduced to the hydrocarbon cracking unit may reduce the formation of intermediate sulfur radicals inside the high temperature reaction environment in the hydrocarbon cracking unit, which may reduce or prevent formation of stable sulfur-containing impurities, such as but not limited to carbon disulfide, methyl mercaptan or both. Reducing or eliminating organosulfur compounds may reduce or prevent product streams from being out-of-specification due to high concentrations of sulfur containing impurities and may improve operation of downstream processes and systems.

According to one embodiment presently described, methods for producing olefins may include passing a hydrocarbon feed comprising one or more hydrocarbons to a hydrocarbon cracking unit and passing a hydrogen sulfide containing stream to the hydrocarbon cracking unit. The hydrogen sulfide containing stream may comprise hydrogen sulfide and a dilution gas, and a concentration of hydrogen sulfide gas in the hydrogen sulfide containing stream may be less than or equal to 10,000 ppmw. A flow rate of the hydrogen sulfide containing stream to the hydrocarbon cracking unit may be sufficient to produce a molar concentration of elemental sulfur in the hydrocarbon cracking unit of from 10 ppm to 200 ppm. The methods may further include cracking at least a portion of the hydrocarbon feed in the hydrocarbon cracking unit to produce a cracker effluent, and contacting the cracker effluent with a quench fluid in a quench unit to produce at least a cracked gas and a first pygas, wherein the cracked gas comprises at least one olefin product and the first pygas has a concentration of carbon disulfide less than 50 ppmw, less than 30 ppmw, or even less than 20 ppmw based on the total mass flow rate of the first pygas.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
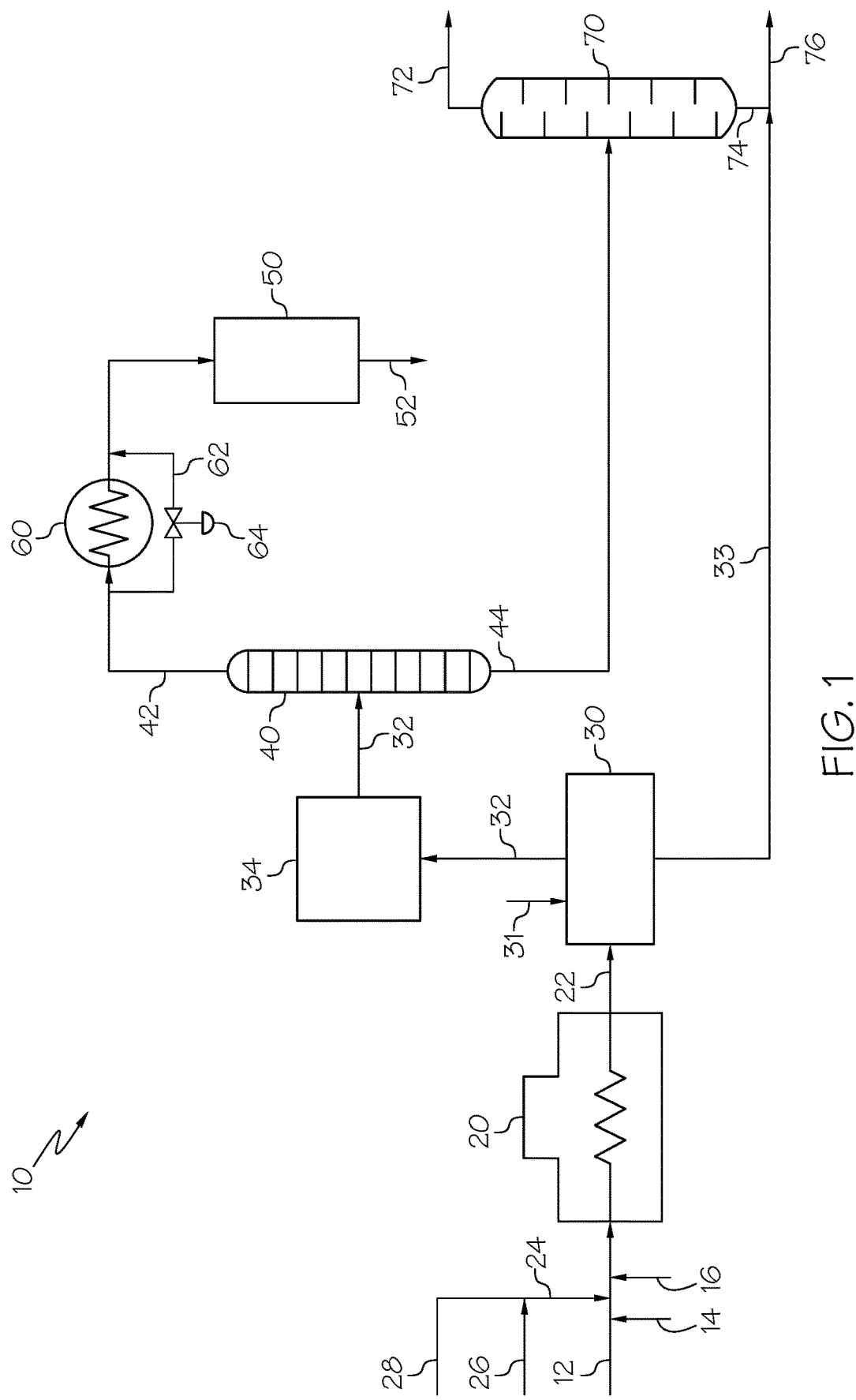
FIG. 1 schematically depicts a process for producing olefins from a hydrocarbon feedstock, according to one or more embodiments shown and described herein.

It should be understood that the drawings are schematic in nature, and may not include some components of reactor systems commonly employed in the art, such as, without limitation, sensors, temperature transmitters, pressure transmitters, flow meters, pumps, valves, heat exchangers, internal reactor structures, and the like. It would be known that these components are within the spirit and scope of the present embodiments disclosed. However, operational components, such as those described in the present disclosure, may be added to the embodiments described in this disclosure.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

One or more embodiments of the present disclosure are directed to methods and processes for producing olefins to reduce formation of sulfur-containing impurities. In particular, one or more embodiments of the present disclosure are directed to methods for reducing formation of carbon disulfide during steam cracking by replacing at least a portion of the dimethyl disulfide introduced to the steam cracking unit with hydrogen sulfide. Referring to FIG. 1, a method for producing olefins can include passing a hydrocarbon feed 12 comprising one or more hydrocarbons to a hydrocarbon cracking unit 20 and passing one or more sulfur-containing compounds to the hydrocarbon cracking unit 20. The sulfur-containing compounds may include at least hydrogen sulfide gas, and a flow rate of the sulfur-containing compounds to the hydrocarbon cracking unit 20 may be sufficient to create a molar concentration of elemental sulfur in the hydrocarbon cracking unit 20 of 10 ppm to 200 ppm. The method may further include cracking at least a portion of the hydrocarbon feed 12 in the hydrocarbon cracking unit 20 to produce a cracker effluent 22 and contacting the cracker effluent 22 with a quench fluid 31 in a quench unit 30 to produce at least a cracked gas 32 and a first pygas 33. The cracked gas 32 may include at least one olefin product, and the first pygas 33 may have a concentration of carbon disulfide less than 50 ppmw, less than 30 ppmw, or even less than 20 ppmw based on the total mass flow rate of the first pygas 33. The at least one olefin product may include but is not limited to ethylene, propylene, butenes, or combinations of these.

In embodiments, the method may further include passing at least a portion of the cracked gas 32 to a cracked gas separation system 40 that separates the cracked gas into at least a hydrogenation feed 42 comprising acetylene, carbon monoxide, hydrogen, and the at least one olefin product and a cracked gas bottom stream 44 comprising at least pyrolysis gasoline components. The cracked gas bottom stream 44 may be passed to a pygas separation system 70 that separates the cracked gas bottom stream 44 into a second pygas 74 and at least one light boiling stream 72. The second pygas 74 may have a concentration of carbon disulfide less than 50 ppmw, less than 30 ppmw, or even less than 20 ppmw based on the total mass flow rate of the second pygas 74.

Figure 8:
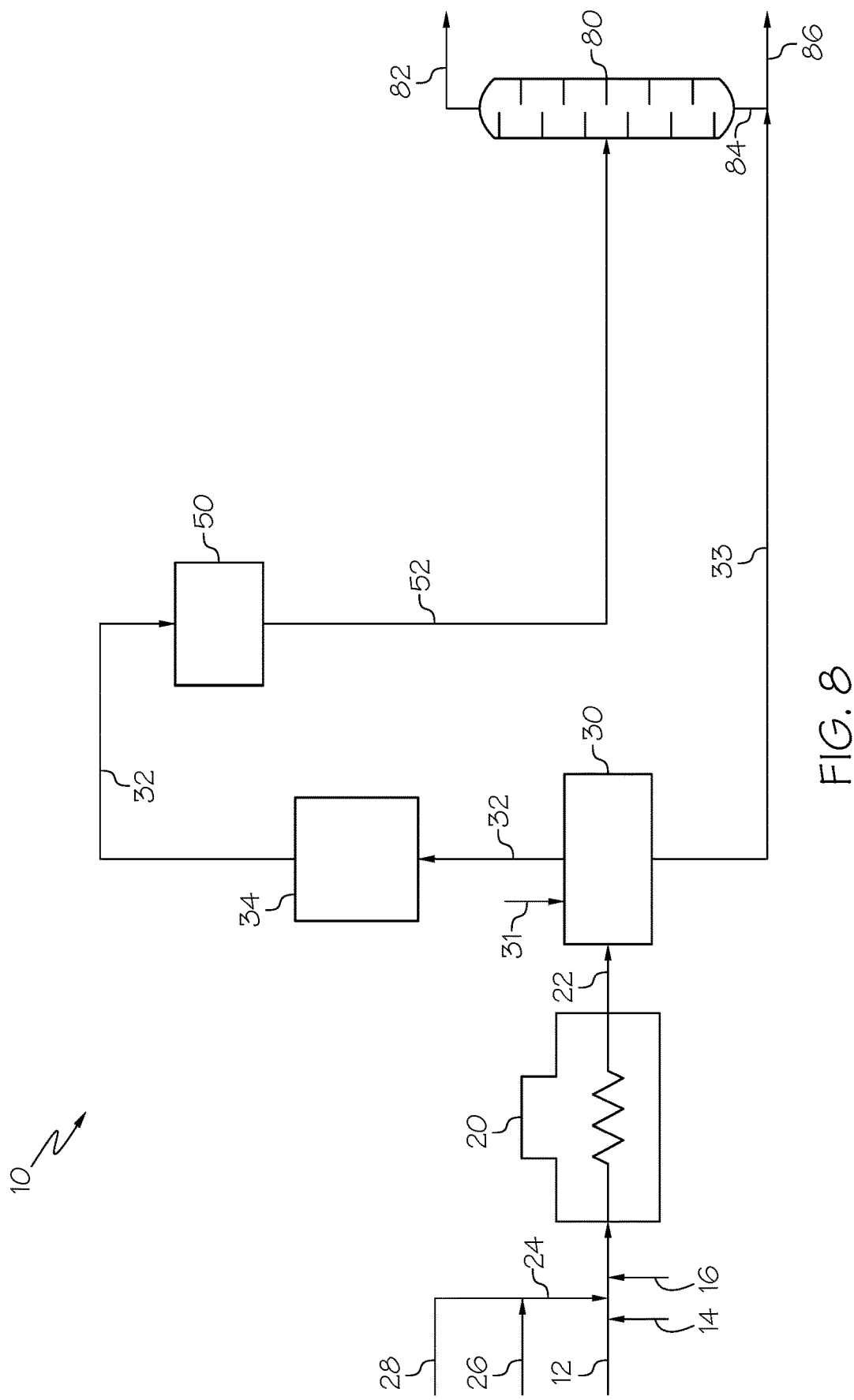
FIG. 8 graphically depicts schematically depicts another process for producing olefins from a hydrocarbon feedstock, according to one or more embodiments shown and described herein.

Referring to FIG. 8, alternatively, in embodiments, the method may include passing the cracked gas 32 to an acetylene hydrogenation unit 50 as the hydrogenation feed to the acetylene hydrogenation unit 50 without separating cracked gas 32, and contacting the cracked gas 32 with an acetylene hydrogenation catalyst in an acetylene hydrogenation unit 50, the contacting causing hydrogenation of at least a portion of the acetylene in the cracked gas 32 to produce a hydrogenation effluent 52. The method may further include passing the hydrogenation effluent 52 to a hydrogenation effluent separation system 80 that separates the hydrogenation effluent 80 into a third pygas 84 and at least one product stream 82 comprising ethylene, propylene, butenes, or combinations of these. The third pygas 84 may have a concentration of carbon disulfide less than 50 ppmw, less than 30 ppmw, or even less than 20 ppmw based on the total mass flow rate of the third pygas 84.

The introduction of hydrogen sulfide to the hydrocarbon cracking unit 20 to replace a portion or all of the organosulfur compounds passed thereto may allow for passivation of the internal furnace coils of the hydrocarbon cracking unit 20 while at the same time may reduce the formation of carbon disulfide and other sulfur-containing impurities. Reducing or eliminating the formation of carbon disulfide and other sulfur-containing impurities may reduce or prevent the occurrence of out-of-specification pygas streams (such as the first pygas 33, second pygas 74, or third pygas 84) from the hydrocarbon cracking process and may reduce or prevent problems in downstream processes caused by the presence of carbon disulfide and other sulfur-containing impurities.

As used herein, the term "hydrogenation feed" refers to an effluent from the cracked gas separation system 40 passed to the acetylene hydrogenation unit 50 that includes at least 95% by mass of the acetylene from the cracked gas 32 introduced to the cracked gas separation system 40. In embodiments, the hydrogenation feed may be the cracked gas 32 passed to the acetylene hydrogenation unit 50 directly without separation upstream of the acetylene hydrogenation unit 50.

As used herein, the term "cracked gas bottom stream" refers to an effluent stream from the cracked gas separation system 40 that is depleted in acetylene, such as including less than 5% by mass of the acetylene from the cracked gas 32 passed to the cracked gas separation system 40.

As used herein, the term "pygas" or "pyrolysis gasoline" may refer to hydrocarbon fractions of the cracking effluent having greater than or equal to 5 carbon atoms. The term "pygas" may be used herein as an abbreviation of pyrolysis gasoline.

As used herein, the term "50% boiling point temperature" may refer to the boiling point temperature at which 50% by weight of the hydrocarbons in a hydrocarbon mixture are transitions from the liquid phase to the vapor phase.

As used herein, the terms "upstream" and "downstream" are relative to the direction of flow of materials through the process. For example, a first unit operation is upstream of a second unit operation if one or more material streams flow from the first unit operation to the second unit operation. The first unit operation is downstream of the second unit operation if one or more material streams flow from the second unit operation to the first unit operation.

As used herein, the term "selectivity" may refer to a ratio of the moles of a desired product to moles of all the products in a reactor effluent. For example, ethylene selectivity of the acetylene hydrogenation unit may be a ratio of the moles of additionally produced ethylene in the hydrogenation effluent divided by the total moles of all the products produced during the hydrogenation reaction. For example, if all acetylene is converted to ethylene, the selectivity is 100%. If all acetylene is converted to ethane, the selectivity is 0 (zero). And if not only all acetylene but also some of incoming ethylene is converted to ethane, the selectivity then becomes negative.

As used herein, the term "breakthrough" may refer to passing of a specific reactant, such as but not limited to, acetylene, methyl acetylene, propadiene, or other compound, from one processing unit to another downstream processing unit in an amount greater than a threshold value specified by the olefin users, for example 2 parts per million by volume (ppmv). In an example, breakthrough may occur when the specific reactant undergoes substantially incomplete conversion in a reaction system so that an effluent passed out of the reaction system has a concentration of the specific reactant of greater than 2 part per million by volume (ppmv), or greater than 1 ppmv depending on olefin users and the location.

As used herein, the term "thermal runaway" may refer to a condition of a process in which an incremental increase in temperature of the process changes the operating conditions in a manner that produces or generates heat, which further increases the temperature.

Referring to FIG. 1, a process 10 for producing olefins through hydrocarbon steam cracking is schematically depicted. The process 10 may include a hydrocarbon cracking unit 20, a quench unit 30 downstream of the hydrocarbon cracking unit 20, a cracked gas treatment system 34, a cracked gas separation system 40 downstream of the quench unit 30 and cracked gas treatment system 34, and an acetylene hydrogenation unit 50 downstream of the cracked gas separation system 40. The acetylene hydrogenation unit 50 may be positioned to receive a hydrogenation feed 42 from the cracked gas separation system 40. A hydrocarbon feedstock 12 may be introduced to the hydrocarbon cracking unit 20 for cracking one or more constituents of the hydrocarbon feedstock 12 to produce one or more olefins. The hydrocarbon feedstock 12 may be any hydrocarbon stream, such as a product stream from a petrochemical process or a refining operation for crude oil, shale gas, or other hydrocarbon sources. In embodiments, the hydrocarbon feedstock 12 may include a plurality of different hydrocarbon streams combined prior to or in the hydrocarbon cracking unit 20. In some embodiments, the hydrocarbon feedstock 12 may be a light hydrocarbon feedstock, such as a feedstock including ethane, propane, butanes, naphtha, other light hydrocarbon, or combinations of these.

The hydrocarbon cracking unit 20 may be operable to receive the hydrocarbon feedstock 12 and crack one or more constituents of the hydrocarbon feedstock 12 to produce a cracker effluent 22. The hydrocarbon cracking unit 20 may be a steam cracking unit, in which the hydrocarbon feedstock 12 is contacted with steam at temperatures of from 500° C. to 850° C. to produce the cracker effluent 22. In embodiments, the hydrocarbon cracking unit 20 may be a steam cracking unit, and the hydrocarbon feedstock 12 may be a light hydrocarbon composition that may include ethane, propane, naphtha, or combinations of these, as well as other hydrocarbons.

The ethane, propane, naphtha, and other hydrocarbons may be steam cracked in the hydrocarbon cracking unit 20 to produce at least ethylene. The hydrocarbon cracking unit 20 may be operated under conditions (i.e., temperature, pressure, gas hourly space velocity, etc.) sufficient to produce one or more light olefins, such as ethylene and propylene, from the hydrocarbons in the hydrocarbon feedstock 12. In embodiments, the hydrocarbon cracking unit 20 may be operated at a temperature of from 500° C. to 850° C., from 500° C. to 810° C., from 550° C. to 850° C., from 550° C. to 810° C., from 600° C. to 850° C., or from 600° C. to 810° C. The temperature of the hydrocarbon cracking unit 20 may depend on the composition of the hydrocarbon feedstock 12 introduced to the hydrocarbon cracking unit 20. Other suitable operating conditions for hydrocarbon cracking processes are well known in the art.

The hydrocarbon cracking unit 20 may include an internal furnace coil. Under the reaction conditions in the hydrocarbon cracking unit 20, some hydrocarbons from the hydrocarbon feed 12 may react to form coke, which may deposit on the surfaces of the internal furnace coil of the hydrocarbon cracking unit 20. Over time, the coke may build up on the surfaces of the internal furnace coil, and this coke buildup may reduce the lifespan of the internal furnace coil in the hydrocarbon cracking unit 20. Sulfur-containing compounds, methanol, or both, can be introduced to the hydrocarbon cracking unit 20 to reduce coke formation. The sulfur-containing compounds may be introduced to the hydrocarbon cracking unit 20 through sulfur compound stream 14. Methanol may be introduced to the hydrocarbon cracking unit 20 through methanol stream 16. The sulfur-containing compounds in the sulfur compound stream 14 may passivate the internal furnace coils in the steam cracking furnace of the hydrocarbon cracking unit 20 to manage the formation of coke in the hydrocarbon cracking unit 20. Increasing or decreasing the amount of sulfur-containing compounds introduced to the hydrocarbon cracking unit 20 may also change the amount of CO generated in the hydrocarbon cracking unit 20, thereby changing the CO concentration in the cracker effluent 22. In conventional hydrocarbon cracking processes for producing olefins, the sulfur compound stream 14 introduced to the hydrocarbon cracking unit 20 most often includes organosulfur compounds, such as but not limited to dimethyl disulfide (DMDS), dimethyl sulfide (DMS), diethyl disulfide (DEDS), diethyl sulfide (DES), methyl mercaptan (MM), or combinations thereof.

The cracker effluent 22 may include one or more cracking reaction products, such as, but not limited to, one or more olefin products such as ethylene, propylene, butenes (e.g., 1-butene, trans-2-butene, cis-2-butene, isobutene); one or more light hydrocarbon gases such as ethane, propane, butanes, pentanes, pentenes, or other light hydrocarbon gases; or combinations of these. The cracker effluent 22 can include pygas components which may have a wide boiling point range of from 200° F. (93° C.) to 800° F. (427° C.), with a 50% boiling point temperature between 325° F. (163° C.) and 375° F. (190° C.). The pygas components can include but are not limited to benzene, toluene, xylenes, styrene, indene, naphthalenes, C10+ hydrocarbons, and other hydrocarbons having greater than or equal to 5 carbon atoms. The cracker effluent 22 can also include hydrogen, CO, acetylene, methyl acetylene, propadiene, methane, hydrogen sulfide, other compounds produced in the hydrocarbon cracking unit 20, unreacted constituents of the hydrocarbon feedstock 12, or combinations of these. For example, the cracking reactions in the hydrocarbon cracking unit 20 may produce byproducts, such as hydrogen and CO, and side-reaction products, such as acetylene, methyl acetylene, propadiene, other side-reaction products, or combinations of these. When organosulfur compounds are introduced to the hydrocarbon cracking unit 20, the cracker effluent 22 may further include sulfur-containing impurities, such as but not limited to carbon disulfide and/or methyl mercaptan, from the decomposition of the organosulfur compounds, such as DMDS, DMS, DEDS, DES, methyl mercaptan, or combinations of these and interaction of the organosulfur compounds with hydrocarbons at high temperatures inside the internal furnace coils. Decomposition of organosulfur compounds and interaction of the organosulfur compounds with hydrocarbons to produce carbon disulfide and other sulfur-containing impurities will be further discussed herein. Additionally, unreacted hydrocarbons and/or other constituents of the hydrocarbon feedstock 12 may pass through the hydrocarbon cracking unit 20 without undergoing reaction so that the cracker effluent 22 includes these unreacted constituents of the hydrocarbon feedstock 12. Acid gases may also be produced in the hydrocarbon cracking unit 20.

Referring still to FIG. 1, the cracker effluent 22 may be passed from the hydrocarbon cracking unit 20 to the quench unit 30 downstream of the hydrocarbon cracking unit 20. The quench unit 30 maybe operable to quench the cracker effluent 22 to reduce the temperature of the cracker effluent 22 and remove steam and heavy hydrocarbon constituents to produce at least a cracked gas 32 and a first pygas 33. Quenching the cracker effluent 22 in the quench unit 30 may separate steam and at least a portion of the heavy hydrocarbon constituents (pygas) from the cracker effluent 22 (e.g., separate the steam and a portion of the heavy hydrocarbons from the gas stream of the cracker effluent 22). The quench unit 30 may include two or more quench units, such as an oil quench unit, a water quench, or both. In embodiments, the quench unit 30 may include a quench water tower that may utilize circulating condensed water as a quench fluid 31 to cool the cracker effluent 22 and recover the heat. The cracker effluent 22 may be cooled by contacting the cracker effluent 22 with the quench fluid 31. Lighter hydrocarbons may be cooled by the quench fluid 31, but may remain in the vapor phase and may pass out of the quench unit 30 as the cracked gas 32. At least a portion of the heavier hydrocarbons having greater boiling point temperatures may condense in the quench unit 30 to form a liquid effluent, which may be passed out of the quench unit 30. When the quench fluid 31 is water, the liquid effluent from the quench unit 30 may be separated to produce the first pygas 33, which may be a liquid stream, and a used quench fluid (not shown). The used quench fluid may be cooled by external heat exchangers and recycled back to the quench unit 30 as at least a portion of the quench fluid 31.

The cracked gas 32 may include hydrocarbons having less than 5 carbon atoms and light gases, such as but not limited to hydrogen, carbon monoxide, hydrogen sulfide, acid gases, nitrogen, or other non-hydrocarbon gases at ambient temperatures. The cracked gas 32 may include constituents from the cracker effluent 22 having atmospheric boiling point temperatures less than 20° C. The cracked gas may include one or more cracking reaction products, such as, but not limited to, one or more olefin products such as ethylene, propylene, and/or butenes (e.g., 1-butene, trans-2-butene, cis-2-butene, isobutene); one or more light hydrocarbon gases, such as ethane, propane, butanes, and/or other light hydrocarbons; or combinations of these. The cracked gas 32 can also include hydrogen, CO, acetylene, methyl acetylene, propadiene, methane, hydrogen sulfide, other compounds produced in the hydrocarbon cracking unit 20, unreacted constituents of the hydrocarbon feedstock 12 having less than 5 carbon atoms, or combinations of these. For example, the cracking reactions in the hydrocarbon cracking unit 20 may produce byproducts, such as hydrogen and CO, and side-reaction products, such as acetylene, methyl acetylene, propadiene, other side-reaction products, or combinations of these. The cracked gas 32 may include at least 95%, at least 98%, or at least 99% of the olefin products, such as ethylene, propylene, and/or butenes, from the cracker effluent 22. The cracked gas 32 may also include at least a portion of the C5+ compounds from the cracker effluent 22 and at least a portion of the pygas components from the cracker effluent 22.

The first pygas 33 may include at least a portion of the C5+ hydrocarbons from the cracker effluent 22. In embodiments, the first pygas 33 may include at least 25%, at least 50%, at least 70%, or even at least 80% by weight of the C5+ hydrocarbons from the cracker effluent 22. The C5+ hydrocarbons in the first pygas 33 may include but are not limited to benzene, toluene, xylenes, indene, styrene, naphthalenes, C10+ hydrocarbons, or combinations of these depending on the nature of the hydrocarbon feed to the hydrocarbon cracking unit 20. The first pygas 33 may comprise carbon disulfide produced in the hydrocarbon cracking unit 20. The first pygas 33 may have less than 50 ppmw carbon disulfide based on the total weight of the first pygas 33. In embodiments, the first pygas 33 may have less than 30 ppmw, less than 20 ppmw, less than 18 ppmw, less than 15 ppmw, or even less than 10 ppmw carbon disulfide based on the total weight of the first pygas 33.

The cracked gas 32 may be passed to a cracked gas treatment system 34, which may include one or more acid gas removal processes, compressors, or both. The cracked gas treatment system 34 may include an acid gas removal process (not shown) to remove acid gases, such as residual hydrogen sulfide and other acid gases, from the cracked gas 32. The cracked gas treatment system 34 may also include one or more compressors (not shown) operable to further reduce the volume of gas before sending the cracked gas 32 to the cracked gas separation system 40 or directly to the acetylene hydrogenation unit 50.

Referring to FIG. 1, the cracked gas 32 may be passed to the cracked gas separation system 40, which may be downstream of the quench section 30 and the cracked gas treatment system 34. The cracked gas separation system 40 may be operable to produce at least the hydrogenation feed 42 and a cracked gas bottom stream 44 from the cracked gas 32. The cracked gas separation system 40 may include one or a plurality of separation units. The cracked gas separation system 40 may be any type of separation system operable to produce the hydrogenation feed 42 from the cracked gas 32. In embodiments, the cracked gas separation system 40 may include a distillation unit in which the cracked gas 32 may be separated into the hydrogenation feed 42 and the cracked gas bottom stream 44 by differences in boiling point temperatures of the constituents. In embodiments, the cracked gas separation system 40 may be a multiple stage distillation column. Separation of the constituents of the cracked gas 32 by differences in boiling point temperature may include initially cooling the cracked gas 32 to temperatures less than the boiling point temperatures of one or more constituents of the cracked gas 32. Thus, the cracked gas separation system 40 may include a condenser operable to condense one or more constituents of the cracked gas 32 upstream of the distillation unit. The cracked gas separation system 40 is not limited to a distillation process. It is understood that other methods and processes for producing the hydrogenation feed 42 from the cracked gas 32 are contemplated.

As previously discussed, the hydrogenation feed 42 may include at least 95% by weight of the acetylene from the cracked gas 32 passed to the cracked gas separation system 40. The hydrogenation feed 42 may include saturated and unsaturated hydrocarbons, such as, but not limited to, ethylene ($C_2H_4$), propylene ($C_3H_6$), acetylene ($C_2H_2$), methyl acetylene ($H_3C$—$C{\equiv}CH$), propadiene ($H_2C{=}C{=}CH_2$), methane ($CH_4$), ethane ($C_2H_6$), propane ($C_3H_8$), or combinations of these. The hydrogenation feed 42 may also include non-hydrocarbon gases, such as, but not limited to, hydrogen, CO, carbon dioxide ($CO_2$), inert gases, or combinations of these. Inert gases may include nitrogen, argon, or other inert gases present in the olefin production system 10. In embodiments, the hydrogenation feed 42 may include acetylene, hydrogen, carbon monoxide, and at least one olefin product. The hydrogenation feed 42 may further include methyl acetylene, propadiene, or both. The product in the hydrogenation feed 42 may include one or more of ethylene, propylene, methane, ethane, propane, or combinations of these.

The cracked gas bottom stream 44 may include less than 5% by weight of the acetylene from the cracked gas 32. The cracked gas bottom stream 44 may include a greater weight percentage of higher boiling point hydrocarbons compared to the hydrogenation feed 42. These higher boiling point hydrocarbons may include the pygas components from the cracked gas 32. The cracked gas bottom stream 44 may also include saturated and unsaturated hydrocarbons, such as, but not limited to propane, propylene, butanes, butenes, butadiene, pentanes, pentenes, or combinations of these depending on the configuration of the cracked gas separation system 40. The cracked gas bottom stream 44 may include the carbon disulfide from the cracked gas 32. The cracked gas bottom stream 44 may include greater than 90%, greater than 95%, greater than 98%, or even greater than 99% of the carbon disulfide from the cracked gas 32.

The cracked gas separation system 40 may be a front end demethanizer (FEDM), a front end depropanizer (FEDP), or a front end de-ethanizer (FEDE). When the cracked gas separation system 40 is an FEDP, the hydrogenation feed 42 may include $C_{3-}$ hydrocarbons and non-hydrocarbon gases. The $C_{3-}$ hydrocarbons may include, but are not limited to, methane, ethane, propane, ethylene, propylene, acetylene, methyl acetylene, propadiene, and combinations of these. The light gases in the hydrogenation feed 42 may include hydrogen, CO, carbon dioxide, nitrogen, or other non-hydrocarbon gases. When the cracked gas separation system 40 is an FEDP, the cracked gas bottom stream 44 may include the C4+ hydrocarbons, such as butanes, butenes, butadiene, pentanes, pentenes (i.e., one or more of the various isomers of pentene), and the pygas components form the cracked gas 32. In embodiments, the cracked gas separation system 40 may be an FEDE or an FEDM, in which case, the greater portions of the propane and propylene may be in the cracked gas bottom stream 44 rather than in the hydrogenation feed 42. In embodiments, when the cracked gas separation system 40 is an FEDE, the cracked gas bottom stream 44 may include the greater fraction of methyl acetylene and propadiene compared to the hydrogenation feed 42. Further information on various front end configurations for acetylene hydrogenation in olefin production processes can be found in "Overview on C2 and C3 Selective Hydrogenation in Ethylene Plants" by Edgar L. Mohundro, 15$^{th}$ Ethylene Produces Conference, 2003 AICHE Spring National Meeting, New Orleans, LA, the entire contents of which are incorporated herein by reference.

Referring again to FIG. 1, the hydrogenation feed 42 may be passed to the acetylene hydrogenation unit 50. The hydrogenation feed 42 may be contacted with a hydrogenation catalyst in the acetylene hydrogenation unit 50. Contacting the hydrogenation feed 42 with the hydrogenation catalyst may produce a hydrogenation effluent, which may include the constituents of the hydrogenation feed 42 and reaction products from the hydrogenation reaction. The contacting of the hydrogenation feed 42 with the hydrogenation catalyst may cause hydrogenation of at least a portion of the acetylene in the hydrogenation feed 42 to produce the hydrogenation effluent 52, which may have a reduced concentration of acetylene compared to the hydrogenation feed 42. The acetylene hydrogenation unit 50 may include one or a plurality of hydrogenation reactors, such as 1, 2, 3, or more than 3 hydrogenation reactors. In embodiments, the acetylene hydrogenation unit 50 may include a plurality of hydrogenation reactors in series, such as a first hydrogenation reactor, a second hydrogenation reactor downstream of the first hydrogenation reactor, and optionally a third hydrogenation reactor downstream of the second hydrogenation reactor. Heat exchangers may be positioned between each of the plurality of hydrogenation reactors of the acetylene hydrogenation unit 50. The hydrogenation reactors of the acetylene hydrogenation unit 50 may be fixed bed reactors comprising a fixed bed of the hydrogenation catalyst. The hydrogenation reactors of the acetylene hydrogenation unit 50 may be vapor phase reactors operable to conduct the hydrogenation reaction through contact of the hydrogenation catalyst (a solid) with reactants in the vapor phase.

The hydrogenation catalyst may be an acetylene hydrogenation catalyst that is a catalyst selective for hydrogenating acetylene relative to product compounds in the hydrogenation feed 42. The hydrogenation catalyst may be any known catalyst for selectively hydrogenating acetylene. Commercial catalysts for acetylene hydrogenation are widely available, and the present disclosure is not limited to any specific composition recited herein. The acetylene hydrogenation unit 50 can be operated at conditions under which the catalytic hydrogenation is selective for hydrogenation of acetylene over hydrogenation of propylene and ethylene. The operating temperature of the acetylene hydrogenation unit 50 may be from 10° C. to 200° C., such as from 10° C. to 100° C., although the operating temperature of the acetylene hydrogenation unit 50 may depend on the composition of the hydrogenation feed 42. Referring to FIG. 1, the olefin production process 10 may include a heat exchanger 60 disposed between the cracked gas separation system 40 and the acetylene hydrogenation unit 50. The heat exchanger 60 may include the bypass 62 having a control valve 64. The temperature of the hydrogenation feed 42 at the inlet of the acetylene hydrogenation unit 50 may be increased or decreased by controlling the amount of the hydrogenation feed 42 passing through the heat exchanger 60 and the amount of the hydrogenation feed 42 bypassing the heat exchanger 60 through the bypass 62. The acetylene hydrogenation unit 50 may operate at a pressure of from 100 pounds per square inch gauge (psig) to 1000 psig (i.e., about 690 kilopascals (kPa) to about 6900 kPa). The acetylene hydrogenation unit 50 may additionally operate at a gas hourly space velocity (GHSV) of from 1,000 to 14,000 (volume per volume of catalyst per hour).

The hydrogenation effluent 52 may refer to the effluents or compositions passed out of the acetylene hydrogenation unit 50, such as out of the last hydrogenation reactor of the acetylene hydrogenation unit 50. The hydrogenation effluent 52 may have an acetylene concentration less than the acetylene concentration of the hydrogenation feed 42. The hydrogenation effluent 52 may have an acetylene concentration of less than or equal to 2 part per million by volume (ppmv), less than or equal to 1 ppmv, less than or equal to 0.5 ppmv, or even less than or equal to 0.1 ppmv. The hydrogenation reaction in the acetylene hydrogenation unit 50 may consume hydrogen from the hydrogenation feed 42, but the change in concentration of hydrogen in the hydrogenation effluent 52 compared to the hydrogenation feed 42 may be less than the detection limits of analytical instruments due to the small concentrations of acetylene in the hydrogenation feed 42 (e.g., in the parts per million range). The hydrogenation catalyst and operating conditions of the acetylene hydrogenation unit 50 may be selective for hydrogenating acetylene relative to hydrogenation of product compounds, such as propylene and ethylene, produced in the hydrocarbon cracking unit 20.

Referring again to FIG. 1, the cracked gas bottom stream 44 may be passed from the cracked gas separation system 40 to a cracked gas bottoms separation system 70 that may be operable to separate the cracked gas bottom stream 44 into one or more lighter boiling streams 72 and the second pygas 74. The cracked gas bottoms separation system 70 may be in fluid communication with the cracked gas separation system 40 so that the cracked gas bottom stream 44 may be passed directly from the cracked gas separation system 40 to the cracked gas bottoms separation system 70. The cracked gas bottoms separation system 70 may include one or a plurality of separation units. The cracked gas bottoms separation system 70 may separate the cracked gas bottom stream 44 into one or a plurality of lighter boiling streams 72 and the second pygas 74. The lighter boiling stream 72 may include constituents of the cracked gas bottom stream 44 that are not pygas components, such as hydrocarbons having less than 5 carbon atoms, hydrocarbons having boiling point temperatures less than 200° F. (93° C.), or both. In embodiments, the cracked gas bottoms separation system 70 may be a debutanizer and the light boiling stream 72 may include C4 hydrocarbons, such as butanes and butenes, and any C3– constituents remaining in the cracked gas bottom stream 44. The light boiling stream 72 may include at least 90%, at least 95%, at least 98%, or even at least 99% by weight of the C4 hydrocarbons from the cracked gas bottom stream 44. The second pygas 74 may include C5+ hydrocarbons from the cracked gas bottom stream 44. In embodiments, the second pygas 74 may include at least 95%, at least 98%, or even at least 99% by weight of the C5+ hydrocarbons from the cracked gas bottom stream 44. The second pygas 74 may include carbon disulfide produced in the hydrocarbon cracking unit 20. The second pygas 74 may include at least 90%, at least 95%, at least 98%, or even at least 99% of the carbon disulfide from the cracked gas bottom stream 44. The second pygas 74 may have less than 50 ppmw carbon disulfide based on the total weight of the second pygas 74. In embodiments, the second pygas 74 may have less than 30 ppmw, less than 20 ppmw, less than 18 ppmw, less than 15 ppmw, or even less than 10 ppmw carbon disulfide based on the total weight of the second pygas 74.

Referring now to FIG. 8, in alternative embodiments, the cracked gas 32 may be passed directly from the quench unit 30 or the cracked gas treatment system 34 to the acetylene hydrogenation unit 50 without a separation system between the cracked gas treatment system 34 and the acetylene hydrogenation unit 50. In these embodiments, the pygas components in the cracked gas may be passed through the acetylene hydrogenation unit 50 and may be separated from the various olefin products downstream of the acetylene hydrogenation unit 50 to produce a third pygas 84.

Referring still to FIG. 8, the system 10 may include a hydrogenation effluent separation system 80 disposed downstream of the acetylene hydrogenation unit 50. The hydrogenation effluent separation system 80 may include one or a plurality of separation units. In embodiments, the hydrogenation effluent separation system 80 may be a debutanizer. The hydrogenation effluent separation system 80 may be operable to separate the hydrogenation effluent 52 into at least one product stream 82 and a third pygas 84. The product stream 82 may include the one or more olefin products, such as ethylene, propylene, butenes, or combinations of these. In embodiments, the hydrogenation effluent separation system 80 may be operable to further separate the hydrogenation effluent 52 into a plurality of product streams 82, such as an ethylene product stream, a propylene product stream, a butene product stream, or combinations of these. The product stream(s) 82 may include at least 95%, at least 98%, or even at least 99% by weight of the ethylene, propylene, or both from the hydrogenation effluent 52. In embodiments, the product stream 82 may include at least 95%, at least 98%, or even at least 99% by weight of the butene from the hydrogenation effluent 52. In embodiments, the product streams 82 may include a C4 hydrocarbon stream. The third pygas 84 may include C5+ hydrocarbons from the hydrogenation effluent 52. In embodiments, the third pygas 84 may include at least 95%, at least 98%, or even at least 99% by weight of the C5+ hydrocarbons from the hydrogenation effluent 52. The third pygas 84 may comprise carbon disulfide produced in the hydrocarbon cracking unit 20. The third pygas 84 may include at least 90%, at least 95%, at least 98%, or even at least 99% of the carbon disulfide from the hydrogenation effluent 52. The third pygas 84 may have less than 50 ppmw carbon disulfide based on the total weight of the third pygas 84. In embodiments, the third pygas 84 may have less than 30 ppmw, less than 20 ppmw, less than 18 ppmw, less than 15 ppmw, or even less than 10 ppmw carbon disulfide based on the total weight of the third pygas 84.

Referring again to FIG. 1, as previously discussed, the sulfur-containing compounds introduced to the hydrocarbon cracking unit 20 through sulfur compound stream 14 can include organosulfur compounds, such as but not limited to dimethyl disulfide (DMDS), dimethyl sulfide (DMS), diethyl disulfide (DEDS), diethyl sulfide (DES), methyl mercaptan (MM), or combinations thereof. These organosulfur compounds can reduce coke in the hydrocarbon cracking unit 20 and can also decrease (or control) the amount of carbon dioxide (CO) generated in the hydrocarbon cracking unit 20 to meet the desired concentration of CO in the acetylene hydrogenation unit 50 downstream of the hydrocarbon cracking unit 20. DMDS, DMS, and/or other organosulfur compounds are conventionally used because they are liquids at ambient temperatures and are easily handled to introduce the DMDS, DMS, and/or other organosulfur compounds to the hydrocarbon cracking unit 20. However, organosulfur compounds, such as DMDS and DMS, undergo decomposition under the reaction conditions in the hydrocarbon cracking unit 20. The decomposition of these organosulfur compounds in the hydrocarbon cracking unit 20 at temperatures greater than 500° C. produces sulfur impurities, such as but not limited to carbon disulfide and methyl mercaptan. The following Chemical Reaction 1 and 2 (RXN 1 and RXN 2) provide the side reactions that occur at temperatures greater than 500° C. that convert DMDS to carbon disulfide (RXN 1).

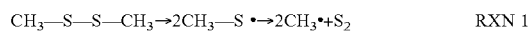

$$CH_3\text{—}S\text{—}S\text{—}CH_3 \rightarrow 2CH_3\text{—}S\bullet \rightarrow 2CH_3\bullet + S_2 \qquad \text{RXN 1}$$

$$2S_2 + CH_4 \rightarrow CS_2 + 2H_2S \qquad \text{RXN 2}$$

As shown in RXN 1, the DMDS ($CH_3$—S—S—$CH_3$) may decompose to sulfur gas and two methyl radicals. As in RXN 2, the sulfur gas may react with methyl groups in the hydrocarbon cracking unit to form the carbon disulfide and hydrogen sulfide.

Referring to FIG. 1, the carbon disulfide may exit the reaction system 10 in the pygas streams, such as the first pygas 33, the second pygas 74, or combined pygas stream 76, which includes a combination of both the first pygas 33 and the second pygas 74. Referring to FIG. 8, the carbon disulfide may exit the reaction system 10 in the first pygas 33, the third pygas 84, or a combined pygas stream 86 comprising both the first pygas 33 and the third pygas 84. The carbon disulfide produced in the hydrocarbon cracking unit 20 may cause the first pygas 33, the second pygas 74, the third pygas 84, of the combined pygas streams 76, 86, to be out-of-specification. The first pygas 33, the second pygas 74, the third pygas 84, or the combined pygas streams 76, 86, may have a specification that calls for a concentration of carbon disulfide of less than 50 ppmw, less than 30 ppmw, or even less than 20 ppmw based on the weight of the first pygas 33, the second pygas 74, the third pygas 84, or combined pygas stream 76, 86, respectively. The use of DMDS to passivate the internal furnace coils of the hydrocarbon cracking unit 20 may result in an out-of-specification concentration of carbon disulfide in the first pygas 33, the second pygas 74, the third pygas 84, or combined pygas stream 76, 86, such as a concentration of carbon disulfide of greater than 50 ppmw, less than 30 ppmw, or even less than 20 ppmw based on the total weight of the pygas stream (first pygas 33, second pygas 74, third pygas 84, combined pygas stream 76, 86, respectively). The carbon disulfide in the first pygas 33, the second pygas 74, the third pygas 84, or combined pygas stream 76, 86, of greater than 50 ppmw may cause problems with downstream processes or applications of these pygas streams.

Decomposition of DMDS in the presence of hydrogen may also produce methyl mercaptan through the Chemical Reaction 3 (RXN 3). In the presence of the hydrogen, the intermediate mercaptomethyl radicals ($CH_3$—S) may react with the hydrogen to produce methyl mercaptan. The methyl mercaptan produced in the hydrocarbon cracking unit 20 may exit the system downstream of the acetylene hydrogenation unit 50 in one or more product streams, such as product stream 72, in the acetylene-depleted effluent 44 from the cracked gas separation system 40, or both. The methyl mercaptan may cause the product streams to be out-of-specification and may cause problems in downstream processes.

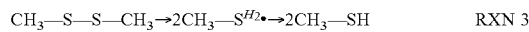

$$CH_3\text{—}S\text{—}S\text{—}CH_3 \rightarrow 2CH_3\text{—}S^{H_2}\bullet \rightarrow 2CH_3\text{—}SH \qquad \text{RXN 3}$$

The systems 10 and processes disclosed herein are directed at reducing the formation of sulfur-containing impurities in the first pygas 33, the second pygas 74, or both. Referring again to FIG. 1, the systems 10 and processes disclosed herein include replacing at least a portion of the organosulfur compounds from the sulfur-containing composition 14 with a hydrogen sulfide containing stream 24. Hydrogen sulfide gas exhibits a passivating effect on the internal furnace coils of the hydrocarbon cracking unit 20 but results in reduced formation of carbon disulfide compared to using DMDS and other organosulfide compounds. Therefore, replacing all or a portion of the organosulfur compounds, such as DMDS, with a hydrogen sulfide containing stream 24 may have the effect of reducing coke formation in the hydrocarbon cracking unit 20 while at the same time reducing the formation of carbon disulfide in the hydrocarbon cracking unit 20. Replacing all or a portion of the organosulfur compounds with the hydrogen sulfide in the hydrogen sulfide containing stream 24 may maintain the concentration of carbon disulfide in the first pygas 33, the second pygas 74, or both, at less than 50 ppmw, less than 30 ppmw, or even less than 20 ppmw.

The hydrogen sulfide containing stream 24 may be added directly to the hydrocarbon cracking unit 20 or may be combined with the hydrocarbon feed 12 upstream of the hydrocarbon cracking unit 20. In embodiments, the hydrogen sulfide containing stream 24 may be in fluid communication with the hydrocarbon cracking unit 20 to pass the hydrogen sulfide containing stream 24 directly to the hydrocarbon cracking unit 20. The hydrogen sulfide containing stream 24 may include hydrogen sulfide gas ($H_2S$) 26 and a dilution gas 28. The dilution gas 28 may be a gas that does not undergo a high degree of cracking in the hydrocarbon cracking unit 20. For example, the dilution gas 28 may be a product compound produced through hydrocarbon cracking. The dilution gas 28 may include but is not limited to one or more of ethane, propane, butanes, or combinations of these.

Referring again to FIG. 1, the hydrogen sulfide gas 26 and the dilution gas 28 may be combined upstream of the hydrocarbon cracking unit 20 to produce the hydrogen sulfide containing stream 24, which may then be passed to the hydrocarbon cracking unit 20 or combined with the hydrocarbon stream 12. The hydrogen sulfide gas 26 and the dilution gas 28 may be combined upstream of the hydrocarbon cracking unit 20. The dilution gas 28 may include at least a portion of ethane, propane, butanes, or combinations of these, recovered from the system 10, such as produced from the cracked gas separation system 40, the hydrogenation effluent separation system 70, or both, and recycled back into combination with the hydrogen sulfide gas 26 to produce the hydrogen sulfide containing stream 24.

The hydrogen sulfide containing stream 24 may have a concentration of hydrogen sulfide sufficient to passivate the internal furnace coils of the hydrocarbon cracking unit 20 and maintain the concentration of carbon disulfide in the first pygas 33, the second pygas 74, or both to less than 50 ppmw, less than 30 ppmw, or even less than 20 ppmw. The concentration of hydrogen sulfide in the hydrogen sulfide containing stream 24 may be less than or equal to 10,000 ppmv, less than or equal to 5,000 ppmv, or even less than or equal to 3,000 ppmv based on the total volume of the hydrogen sulfide containing stream 24. The concentration of hydrogen sulfide in the hydrogen sulfide containing stream 24 may be greater than or equal to 10 ppmv, greater than or equal to 100 ppmv, or even greater than or equal to 1,000 ppmv based on the total volume of the hydrogen sulfide containing stream 24. The concentration of hydrogen sulfide in the hydrogen sulfide containing stream 24 may be from 10 ppmv to 10,000 ppmv, from 100 ppmv to 5000 ppmv, from 500 ppmv to 4000 ppmv, or from 1000 ppmv to 3000 ppmv. In embodiments, the hydrogen sulfide containing stream 24 may not include compounds comprising both carbon and sulfur in the same molecule. In embodiments, the hydrogen sulfide containing stream does not include DMDS, DMS, DEDS, DES, methyl mercaptan, or combinations of these.

The hydrogen sulfide containing stream 24 may include less than 10 ppmv compounds comprising both carbon and sulfur in the same molecule based on the total weight of the hydrogen sulfide containing stream 24. In embodiments, the hydrogen sulfide containing stream 24 comprises less than 10 ppmv DMDS, DMS, DEDS, DES, methyl mercaptan, or combinations of these.

Figure 2:
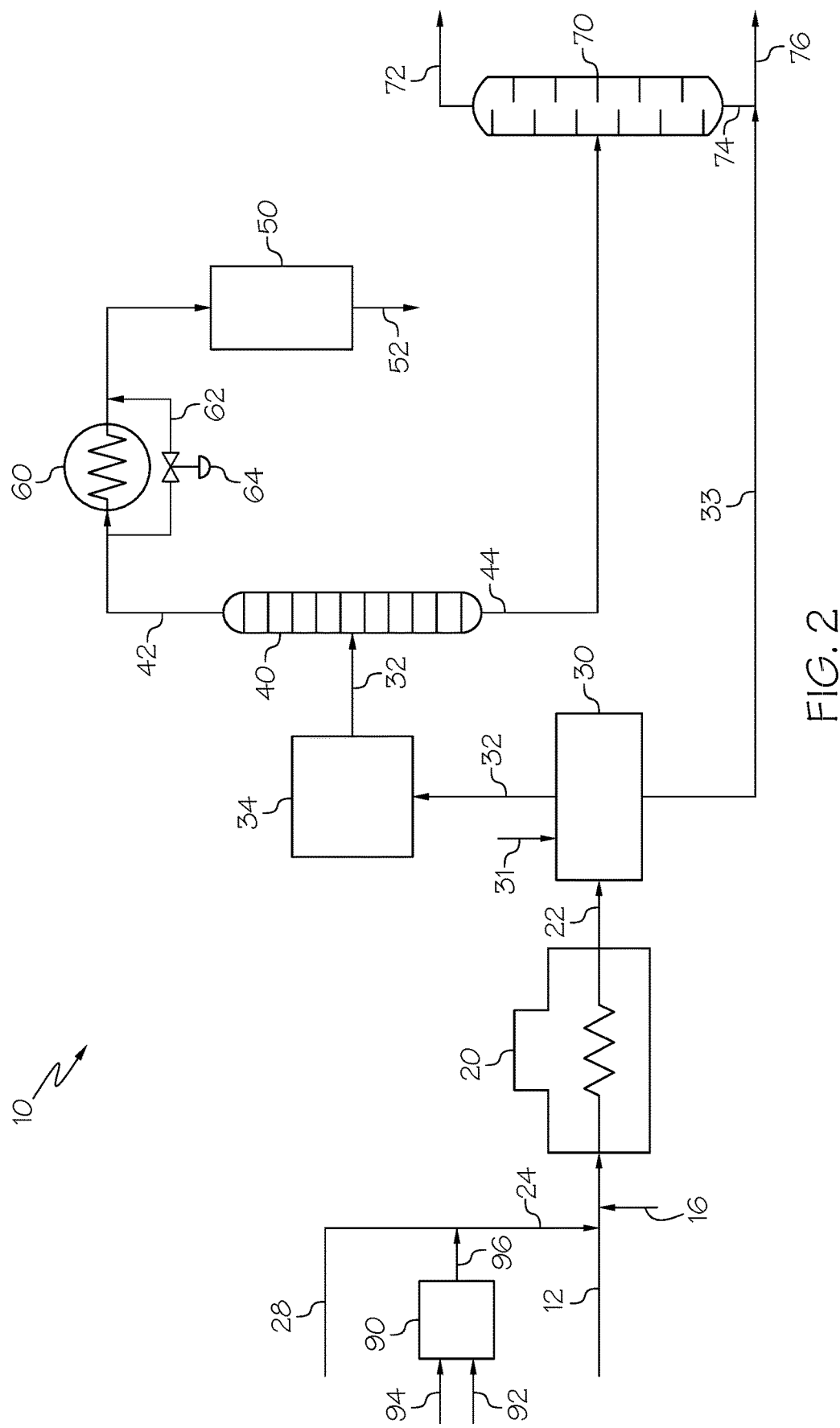
FIG. 2 schematically depicts another process for producing olefins from a hydrocarbon feedstock, according to one or more embodiments shown and described herein.

Referring now to FIG. 2, in embodiments, the hydrogen sulfide gas may be produced through catalytic decomposition of DMDS, DMS, or other organosulfur compound under mild reaction conditions in a catalytic decomposition unit 90 disposed upstream of the hydrocarbon cracking unit 20. The mild reaction conditions of the catalytic decomposition unit 90 may include reaction temperatures less than 350° C., which are substantially less severe than the reaction temperatures of greater than 500° C. in the hydrocarbon cracking unit 20, which can lead to formation of carbon disulfide. Decomposition of organosulfur compounds such as DMDS and/or DMS in the catalytic decomposition unit 90 operated at less severe reaction conditions (e.g., T<350° C.) compared to the hydrocarbon cracking unit 20 may enable decomposition of the organosulfur compounds to produce hydrogen sulfide and alkanes without producing carbon disulfide. In embodiments, an organosulfur compound stream 92 may comprise DMDS, DMS, or both. Contacting DMDS ($CH_3$—S—S—$CH_3$) with hydrogen 94 in the presence of the hydrotreating catalyst at the reduced severity operating conditions may cause the DMDS to decompose according to the following Chemical Reaction 4 (RXN 4).

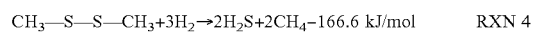

$$CH_3-S-S-CH_3 + 3H_2 \rightarrow 2H_2S + 2CH_4 - 166.6 \text{ kJ/mol} \qquad \text{RXN 4}$$

Contacting DMS with hydrogen 94 in the presence of the hydrotreating catalyst at the reduced severity operating conditions may cause the DMS ($CH_3$—S—$CH_3$) to decompose according to the following Chemical Reaction 5 (RXN 5).

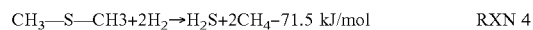

$$CH_3-S-CH3 + 2H_2 \rightarrow H_2S + 2CH_4 - 71.5 \text{ kJ/mol} \qquad \text{RXN 4}$$

As shown in RXN 4 and RXN 5, at the lower temperatures of less than 350° C., DMDS and DMS can be decomposed into hydrogen sulfide and methane without producing carbon disulfide in the presence of a hydrotreating catalyst.

Referring again to FIG. 2, an organosulfur compound stream 92, such as a DMDS stream, may be introduced to the catalytic decomposition unit 90 disposed upstream of the hydrocarbon cracking unit 20. The organosulfur compound stream 92 may be contacted with hydrogen in the presence of a catalyst in the catalytic decomposition unit 90. The hydrogen may be introduced to the hydrotreating reactor 90 through hydrogen stream 94. Contact of the organosulfur compound stream 92 with the hydrogen stream 94 in the presence of the catalyst may cause all or a portion of the organosulfur compounds, such as DMDS, DMS, DEDS, DES, or other organosulfur compounds, to react to produce a catalytic decomposition effluent 96 comprising at least hydrogen sulfide and at least one alkane gas, such as but not limited to methane, ethane, propane, butanes, or combinations of these. Decomposition of DMDS or DMS would produce methane and hydrogen sulfide as shown in RXN 4 and RXN 5. Decomposition of DEDS or DES would produce ethane and hydrogen sulfide. Decomposition of other organosulfide compounds may produce other alkane gases, such as propane or butanes.

The catalyst in the catalytic decomposition unit 90 may be any commercially available hydrotreating catalyst capable of catalyzing the decomposition reaction of DMDS or other organosulfur compounds to produce hydrogen sulfide. In embodiments, the catalyst may include cobalt (Co), molybdenum (Mo), and sulfur supported on an alumina support. Other commercially available hydrotreated catalysts may also be suitable for use in the catalytic decomposition unit 90.

The catalytic decomposition unit 90 may include a fixed bed reactor comprising the catalyst. The catalytic decomposition unit 90 may include one or a plurality of fixed bed reactors operated in series or in parallel. The catalytic decomposition unit 90 may be operated at a reaction temperature sufficient to decompose the DMDS, DMS, or other organosulfur compound from the organosulfur compound stream 92 to produce hydrogen sulfide without producing carbon disulfide. The catalytic decomposition unit 90 may be operated at reaction temperatures less than or equal to 350° C., less than or equal to 300° C., or even less than or equal to 250° C. The catalytic decomposition unit 90 may be operated at reaction temperatures of from 200° C. to 350° C., from 250° C. to 325° C., from 250° C. to 300° C., or about 300° C.

The catalytic decomposition effluent 96 may include hydrogen sulfide and alkane gases such as methane or ethane. The catalytic decomposition effluent 96 may also include unreacted DMDS, DMS, or other organosulfur compounds. The conversion of DMDS, DMS, or other organosulfur compounds in the catalytic decomposition unit 90 may be from 90% to 100% based on the total weight of the organosulfur compounds introduced to the catalytic decomposition unit 90. The catalytic decomposition effluent 96 may be further diluted with a dilution gas 28 to produce the hydrogen sulfide containing stream 24 so that hydrogen sulfide containing stream 24 may have a concentration of hydrogen sulfide of from 10 ppmv to 10,000 ppmv. The dilution gas may be any of the dilution gases previously discussed in this disclosure. The catalytic decomposition unit 90 may also be integrated into the system shown in FIG. 8.

Referring again to FIG. 1, the hydrogen sulfide containing stream 24 may be used as the only sulfur source introduced to the hydrocarbon cracking unit 20 or may be used in combination with the sulfur compound stream 14, which may be introduced separately to the hydrocarbon cracking unit 20. In embodiments, the sulfur compound stream 14 may not be introduced to the hydrocarbon cracking unit 20 so that the hydrogen sulfide containing stream 24 may be the only sulfur introduced to the hydrocarbon cracking unit 20. In embodiments, the feed to the hydrocarbon cracking unit 20 may consist of the hydrocarbon feed 12, the hydrogen sulfide containing stream 24, and, optionally, the methanol-containing stream 16. Alternatively, in embodiments, the hydrogen sulfide containing stream 24 and the sulfur compound stream 14, which may include DMDS, DMS, DEDS, DES, methyl mercaptan, or combinations of these, may both be introduced to the hydrocarbon cracking unit 20. In embodiments, DMDS may be introduced to the hydrocarbon cracking unit 20. However, when the DMDS is introduced to the hydrocarbon cracking unit 20 along with the hydrogen sulfide, the amount of DMDS introduced to the hydrocarbon cracking unit 20 may be less than the amount of DMDS introduced to the hydrocarbon cracking unit 20 without the addition of the hydrogen sulfide containing stream 24. The DMDS may be introduced to the hydrocarbon cracking unit 20 in a DMDS stream (e.g., sulfur compound stream 14) separate from the hydrogen sulfide containing stream 24. Referring again to FIG. 2, in embodiments comprising the catalytic decomposition unit 90, the hydrogen sulfide containing stream 24 may include unreacted DMDS so that DMDS may be introduced to the hydrocarbon cracking unit 20 through the hydrogen sulfide containing stream 24.

During operation of the hydrocarbon cracking unit 20, the proportion of elemental sulfur in the hydrocarbon cracking unit 20 contributed by the hydrogen sulfide gas in the hydrogen sulfide containing stream 24 may be greater than zero %, greater than or equal to 10%, or even greater than or equal to 10% based on the total molar amount of elemental sulfur in the hydrocarbon cracking unit 20. During operation, the proportion of elemental sulfur in the hydrocarbon cracking unit 20 contributed by the hydrogen sulfide gas in the hydrogen sulfide containing stream 24 may be less than or equal to 100%, less than or equal to 90%, less than or equal to 80%, or even less than or equal to 50% based on the total molar amount of elemental sulfur in the hydrocarbon cracking unit 20. During operation, the proportion of elemental sulfur in the hydrocarbon cracking unit 20 contributed by the hydrogen sulfide gas in the hydrogen sulfide containing stream 24 may be from greater than zero % to 100%, from 10% to 100%, from 10% to 100%, from 1% to 90%, from 10% to 90%, or from 10% to 50% based on the total molar amount of elemental sulfur in the hydrocarbon cracking unit 20.

The flow rate of the hydrogen sulfide containing stream 24 or the hydrogen sulfide containing stream 24 and the sulfur compound stream 14 to the hydrocarbon cracking unit 20 may be sufficient to produce a molar concentration of elemental sulfur in the hydrocarbon cracking unit 20 sufficient to passivate the internal furnace coils and reduce coke formation in the hydrocarbon cracking unit 20. The flow rate of the hydrogen sulfide containing stream 24 or the hydrogen sulfide containing stream 24 and the sulfur compound stream 14 to the hydrocarbon cracking unit 20 may be sufficient to produce a molar concentration of elemental sulfur in the hydrocarbon cracking unit 20 from 10 ppm to 200 ppm, from 10 ppm to 100 ppm, from 20 ppm to 200 ppm, or 20 ppm to 100 ppm. When the molar concentration of elemental sulfur in the hydrocarbon cracking unit 20 is less than 10 ppm, the amount of sulfur may be insufficient to passivate the internal furnace coils of the hydrocarbon cracking unit 20 to reduce coke formation. In embodiments, the molar concentration of elemental sulfur in the hydrocarbon cracking unit 20 may be increased or decreased by changing the flow rate of the hydrogen sulfide containing stream 24, the concentration of hydrogen sulfide in the hydrogen sulfide containing stream 24, or both.

Figure 3:
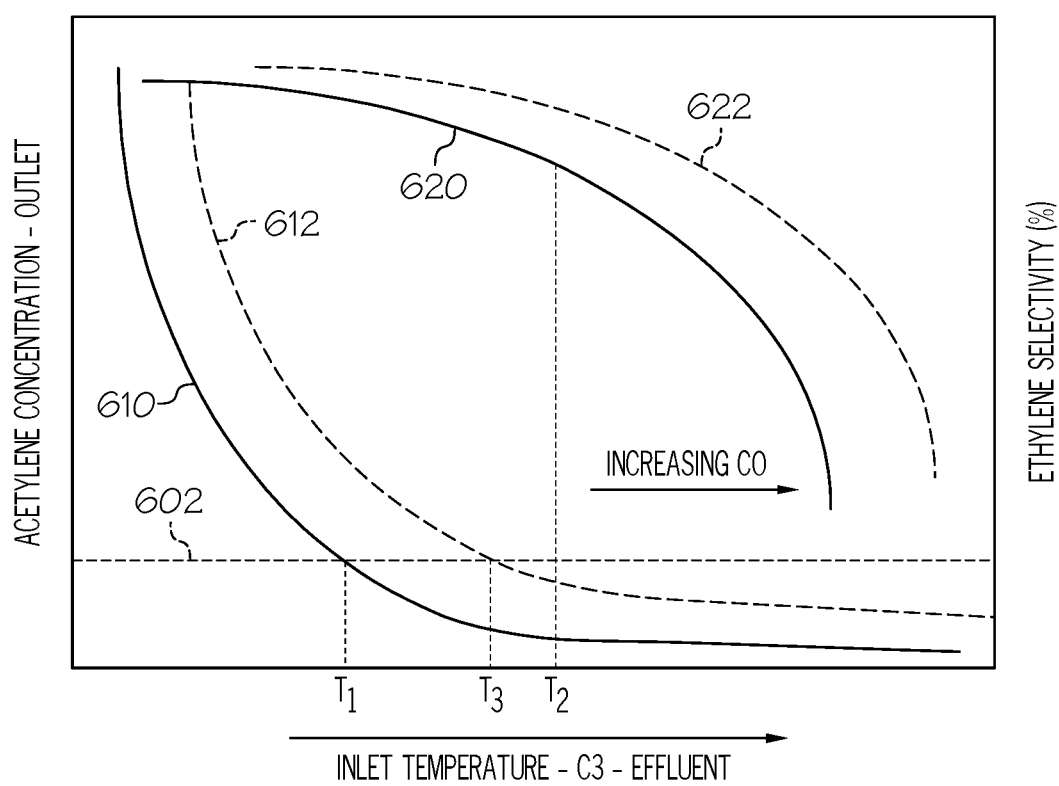
FIG. 3 graphically depicts a concentration of acetylene (y-axis-left) and ethylene selectivity (y-axis-right) for the acetylene hydrogenation unit as a function of a temperature (x-axis) of a hydrogenation feed passed to the acetylene hydrogenation unit, according to one or more embodiments shown and described herein.

Changing the molar concentration of elemental sulfur in the hydrocarbon cracking unit 20 may also influence the amount of carbon monoxide (CO) produced in the hydrocarbon cracking unit 20. The amount of CO produced in the hydrocarbon cracking unit 20 may in turn influence the operating window of the acetylene hydrogenation unit 50 downstream of the hydrocarbon cracking unit 20. Referring now to FIG. 3, an operating window for the inlet temperature of the hydrogenation feed 42 introduced to the acetylene hydrogenation unit 50 for a given composition of the hydrogenation feed 42 can be defined between the inlet temperature $T_1$, below which the acetylene concentration in the hydrogenation effluent 52 is greater than the target acetylene concentration 602, and the inlet temperature $T_2$, above which the ethylene selectivity decreases and hydrogenation of olefin products can result in thermal runaway of the acetylene hydrogenation unit 50.

Referring again to FIG. 3, the process window for operation of the acetylene hydrogenation unit 50 may be modified or shifted by changes in the CO concentration in the acetylene hydrogenation unit 50. Increasing the CO concentration in the acetylene hydrogenation unit 50 may widen the process window and shift the process window for the temperature of the hydrogenation feed 42 towards greater temperatures. In FIG. 3, curve 612 represents the acetylene concentration in the hydrogenation effluent 52 as a function of inlet temperature of the hydrogenation feed 42 for operation of the acetylene hydrogenation unit 50 with an increased concentration of CO compared to the concentration of CO for curve 610. By increasing the concentration of CO in the acetylene hydrogenation unit 50, the inlet temperature $T_3$ of the hydrogenation feed 42, at which the acetylene concentration in the hydrogenation effluent 52 is equal to the target acetylene concentration 602, is greater than the corresponding temperature $T_1$ of the hydrogenation feed 42 for curve 610 (having a lesser concentration of CO).

Increasing the CO concentration in the acetylene hydrogenation unit 50 may also shift the ethylene selectivity curve towards greater inlet temperatures. Curve 622 in FIG. 3 represents the ethylene selectivity for the acetylene hydrogenation unit 50 as a function of time for a greater CO concentration compared to curve 620. As shown in FIG. 3, increasing the CO concentration (curve 622) in the acetylene hydrogenation unit 50 can enable operation of the acetylene hydrogenation unit 50 at greater inlet temperatures compared to operating the acetylene hydrogenation unit 50 with a lesser concentration of CO. Thus, increasing the CO concentration in the acetylene hydrogenation unit 50 can enable operation of the acetylene hydrogenation unit 50 at a greater temperature without causing thermal runaway.

The CO concentration in the hydrogenation feed 42 or the acetylene hydrogenation unit 50 can be increased or decreased by adjusting the amount of CO produced in the hydrocarbon cracking unit 20. The amount of CO produced in the hydrocarbon cracking unit 20 may be adjusted by changing one or more operating parameters of the hydrocarbon cracking unit 20, such as by changing the total concentration of elemental sulfur in the hydrocarbon cracking unit 20. The amount of CO produced in the hydrocarbon cracking unit 20 may be increased or decreased by increasing or decreasing the amount of hydrogen sulfide gas, organosulfur compounds, or both, introduced to the hydrocarbon cracking unit 20. In embodiments, the concentration of CO in the cracked gas 32 may be increased or decreased by increasing or decreasing the concentration of hydrogen sulfide gas in the hydrogen sulfide containing stream 24, the flow rate of the hydrogen sulfide containing stream 24, or both. Alternatively or additionally, in embodiments the concentration of CO in the cracked gas 32 may be increased or decreased by increasing or decreasing an amount of sulfur-containing compounds introduced to the hydrocarbon cracking unit 20, where the sulfur-containing compounds may include, but are not limited to, one or more of dimethyl disulfide (DMDS), dimethyl sulfide (DMS), diethyl disulfide (DEDS), diethyl sulfide (DES), methyl mercaptan (MM), or combination thereof.

Referring again to FIG. 1, a method for producing olefins may include passing the hydrocarbon feed 12 comprising one or more hydrocarbons to the hydrocarbon cracking unit 20 and passing one or more sulfur-containing compounds to the hydrocarbon cracking unit 20. The hydrocarbon feed 12 and the hydrocarbon cracking unit 20 may have any of the features previously discussed herein for the hydrocarbon feed 12 and the hydrocarbon cracking unit 20, respectively. The hydrocarbon cracking unit 20 may be a steam cracking unit. The sulfur-containing compounds may include at least hydrogen sulfide gas. A flow rate of the sulfur-containing compounds to the hydrocarbon cracking unit 20 may be sufficient to create a molar concentration of elemental sulfur in the hydrocarbon cracking unit 20 of from 10 ppmw to 200 ppmw, from 10 ppmw to 100 ppmw, from 20 ppmw to 200 ppmw, or from 20 ppmw to 100 ppmw. The method may further include cracking at least a portion of the hydrocarbon feed 12 in the hydrocarbon cracking unit 20 to produce a cracker effluent 22 and contacting the cracker effluent 22 with a quench fluid 31 in the quench unit 30 to produce at least a cracked gas 32 and a first pygas 33. The quench unit 30 and quench fluid 31 may have any of the features or characteristics previously described herein. The cracked gas 32 may comprise at least one olefin product, such as but not limited to ethylene, propylene, butenes, or combinations of these. The first pygas 33 may have a concentration of carbon disulfide less than 50 ppmw, less than 30 ppmw, or even less than 20 ppmw based on the total mass flow rate of the first pygas 33. The cracked gas 32 and first pygas 33 may have any of the other compositions or features previously described herein for these streams.

Referring to FIG. 1, the method may further include passing at least a portion of the cracked gas 32 to the cracked gas separation system 40 that separates the cracked gas 32 into at least the hydrogenation feed 42 comprising acetylene, carbon monoxide, hydrogen, and at least one olefin product and a cracked gas bottom stream comprising at least pyrolysis gasoline components. The method may further include passing the cracked gas bottom stream 44 to a pygas separation system 70 that may separate the cracked gas bottom stream 44 into a second pygas 74 and at least one light boiling stream 72. The second pygas 74 may have a concentration of carbon disulfide less than 50 ppmw, less than 30 ppmw, or even less than 20 ppmw based on the total mass flow rate of the second pygas 74. The first pygas 33 and the second pygas 74 may be combined to form a combined pygas stream 76, which may have a concentration of carbon disulfide less than 50 ppmw, less than 30 ppmw, or even less than 20 ppmw based on the total mass flow rate of the combined pygas stream 76.

Referring to FIG. 8, in embodiments, the methods may include passing at least a portion of or all of the cracked gas 32 to the acetylene hydrogenation unit 50 as the hydrogenation feed to the acetylene hydrogenation unit 50. The methods may further include contacting the cracked gas 32 with the acetylene hydrogenation catalyst in the acetylene hydrogenation unit 50. The contacting may cause hydrogenation of at least a portion of the acetylene in the cracked gas 32 to produce the hydrogenation effluent 52. The methods may further include passing the hydrogenation effluent 52 to the hydrogenation effluent separation system 80 that may separate the hydrogenation effluent 52 into a third pygas 84 and at least one product stream 82 comprising ethylene, propylene, butenes, or combinations of these. The third pygas 84 may have a concentration of carbon disulfide less than 50 ppmw, less than 30 ppmw, or even less than 20 ppmw based on the total mass flow rate of the third pygas 84. The first pygas 33 and the third pygas 84 may be combined to form a combined pygas stream 86, which may have a concentration of carbon disulfide less than 50 ppmw, less than 30 ppmw, or even less than 20 ppmw based on the total mass flow rate of the combined pygas stream 86.

In any of the methods disclosed herein, passing one or more sulfur-containing compounds to the hydrocarbon cracking unit 20 may include passing the hydrogen sulfide containing stream 24 directly to the hydrocarbon cracking unit 20 or combining the hydrogen sulfide containing stream 24 with the hydrocarbon feed 12 upstream of the hydrocarbon cracking unit 20. The hydrogen sulfide containing stream 24 may include the hydrogen sulfide gas 26 and the dilution gas 28. The dilution gas 28 may include one or more of ethane, propane, butanes, or combinations of these. Any of the methods disclosed herein may include recycling at least a portion of ethane, propane, butanes, or combinations of these, recovered from the cracked gas 32 as at least a portion of the dilution gas 28 for the hydrogen sulfide containing stream 24.

In embodiments, the methods disclosed herein may include passing an organosulfur compound stream 92 and hydrogen (via hydrogen stream 94) to the catalytic decomposition unit 90 disposed upstream of the hydrocarbon cracking unit 20. The methods may further include contacting the organosulfur compound stream 92 and hydrogen in the presence of a catalyst in the catalytic decomposition unit 90 at a reaction temperature less than 350° C., where the contacting causes at least a portion of organosulfur compounds from the organosulfur compound stream 92 to react to produce a catalytic decomposition effluent 96 comprising hydrogen sulfide gas. The catalytic decomposition unit 90 may have any of the features, catalysts, or operating conditions disclosed herein for this unit. The methods may further include passing the catalytic decomposition effluent 96 to the hydrocarbon cracking unit 20 as at least a portion of the hydrogen sulfide containing stream 24. In embodiments, the catalytic decomposition effluent 96 may be combined with the dilution gas 28 to produce the hydrogen sulfide containing stream 24.

In embodiments of any of the methods disclosed herein, the hydrogen sulfide containing stream 24 may not include compounds comprising both carbon and sulfur in the same molecule, such as DMDS, DMS, DEDS, DES, methyl mercaptan, or other organosulfur compounds. In embodiments, the hydrogen sulfide containing stream 24 may include less than 10 ppmv compounds comprising both carbon and sulfur in the same molecule based on the total weight of the hydrogen sulfide containing stream 24. In embodiments, the hydrogen sulfide containing stream 24 may not include dimethyl disulfide, dimethyl sulfide, diethyl sulfide, methyl mercaptan, or combinations of these. The hydrogen sulfide containing stream 24 may have a concentration of hydrogen sulfide gas of less than or equal to 10,000 ppmw or less than 5,000 ppmw, such as from 10 ppmw to 10,000 ppmw, from 100 ppmw to 5,000 ppmw, or from 1,000 ppmw to 3,000 ppmw based on the total weight of the hydrogen sulfide containing stream 24.

Any of the methods described herein may further include increasing or decreasing the concentration of hydrogen sulfide gas in the hydrogen sulfide containing stream 24 or the flow rate of the hydrogen sulfide containing stream 24 to increase or decrease the concentration of elemental sulfur in the hydrocarbon cracking unit 20. Any of the methods described herein may further include increasing or decreasing the concentration of hydrogen sulfide gas in the hydrogen sulfide containing stream 24, the flow rate of the hydrogen sulfide containing stream 24, or both, to increase or decrease a concentration of carbon monoxide in the cracked gas 32. The hydrogen sulfide may passivate the internal furnace coils in the hydrocarbon cracking unit 20 to reduce coke formation.

In embodiments, any of the methods described herein may further include introducing dimethyl disulfide, dimethyl sulfide, diethyl sulfide, methyl mercaptan, or combinations of these to the hydrocarbon cracking unit 20 separate from and in addition to the hydrogen sulfide containing stream 24. The amount of dimethyl disulfide, dimethyl sulfide, diethyl sulfide, methyl mercaptan, or combinations of these introduced to the hydrocarbon cracking unit 20 maybe may be less than an amount of these organosulfur compounds introduce to the hydrocarbon cracking unit 20 in the absence of the hydrogen sulfide containing stream 24. In any of the methods disclosed herein, an amount of elemental sulfur contributed by the hydrogen sulfide gas in the hydrogen sulfide containing stream 24 introduced to the hydrocarbon cracking unit 20 as a percentage of the total elemental sulfur in the hydrocarbon cracking unit 20 may be greater than zero percent and less than or equal to 100%, such as greater than or equal to 10% and less than or equal to 100%, or greater than or equal to 10% and less than or equal to 100%.

EXAMPLES

Embodiments of the present disclosure will be further clarified by the following examples, which should not be construed as limiting on the disclosed and/or claimed embodiments presently described.

Comparative Examples 1 and 2

In Comparative Example 1, an in-house kinetic model is used to calculate the carbon disulfide ($CS_2$) concentration in pygas resulting from propane cracking with addition of 100 ppmv DMDS to the hydrocarbon cracking unit. In Comparative Example 2, the same kinetic model is used to calculate the $CS_2$ concentration in pygas resulting from ethane cracking with addition of 100 ppmv DMDS to the hydrocarbon cracking unit. The hydrocarbon cracking unit is a steam cracking unit. The calculations are conducted using custom-built modeling software that enables simulations of sulfur impurities decomposition/formation during steam cracking reactions. The concentration of carbon disulfide in the cracker effluent, the fraction of the cracker effluent separated out as the first pygas, and the concentration of carbon disulfide in the first pygas are calculated and the results are provided below in Table 1.

Examples 3-6

In Examples 3-6, the effects of replacing a portion of DMDS with hydrogen sulfide gas are studied. In Examples 3 and 4, the in-house kinetic model is used to calculate the $CS_2$ concentration in pygas resulting from propane cracking with replacement of 50% and 100%, respectively, of the DMDS passed to the hydrocarbon cracking unit with hydrogen sulfide gas ($H_2S$) while maintaining the molar concentration of total elemental sulfur in the hydrocarbon cracking unit constant. In Examples 5 and 6, the in-house kinetic model is used to calculate the $CS_2$ concentration in pygas resulting from ethane cracking with replacement of 50% and 100%, respectively, of the DMDS passed to the hydrocarbon cracking unit with $H_2S$ gas while maintaining the molar concentration of total elemental sulfur in the hydrocarbon cracking unit constant. The results of the modeling for Comparative Examples 1 and 2 and Examples 3-6 are provided below in Table 1.

TABLE 1

|  | Propane Steam Cracking | | | Ethane Steam Cracking | | |
| --- | --- | --- | --- | --- | --- | --- |
|  | Comp Ex. 1 | Example 3 | Example 4 | Comp. Ex. 2 | Example 5 | Example 6 |
| Sulfur from DMDS (ppmv) | 100 | 50 | 0 | 100 | 50 | 0 |
| Sulfur from H$_2$S (ppmv) | 0 | 100 | 200 | 0 | 100 | 200 |
| Total Sulfur (ppmv) | 200 | 200 | 200 | 200 | 200 | 200 |
| CS$_2$ Concentration in Cracker Effluent (ppmw) | 0.73 | 0.52 | 0.32 | 1.53 | 1.30 | 1.18 |
| Pygas Fraction in Cracker Effluent (wt. %) | 2.60 | 2.60 | 2.60 | 1.70 | 1.70 | 1.70 |
| CS$_2$ Concentration in pygas (ppmw) | 28 | 20 | 12 | 90 | 76 | 69 |

As Table 1 shows, for a typical propane steam cracking, the CS$_2$ concentration in the pygas is predicted to be around 28 ppmw when 100 ppmv DMDS is added to the feedstock, as in Comparative Example 1. If 50% of the DMDS is replaced by H$_2$S gas while keeping the molar concentration of total elemental sulfur constant (i.e., at 200 ppm) as in Example 3, the CS$_2$ concentration in the pygas is reduced to 20 ppmw. If all of the DMDS is replaced by H$_2$S while keeping the molar concentration of total elemental sulfur constant at 200 ppmv as in Example 4, then CS$_2$ concentration in the pygas is further reduced to 12 ppmw, which is a 57% decrease in CS$_2$ concentration compared to steam cracking propane with only DMDS added to the hydrocarbon cracking unit as in Comparative Example 1.

For a typical ethane steam cracking, the CS$_2$ concentration in the pygas is predicted to be around 90 ppmw when 100 ppmv DMDS is added to the feedstock, as in Comparative Example 2. If 50% of the DMDS is replaced by H$_2$S gas while keeping the molar concentration of total elemental sulfur constant (i.e., at 200 ppm) as in Example 5, the CS$_2$ concentration in the pygas is reduced to 76 ppmw. If all of the DMDS is replaced by H$_2$S while keeping the molar concentration of total elemental sulfur constant at 200 ppmv as in Example 6, then CS$_2$ concentration in the pygas is further reduced to 69 ppmw, which is a 23% decrease in CS$_2$ concentration compared to ethane steam cracking with only DMDS added to the hydrocarbon cracking unit as in Comparative Example 1. The reduction in concentration of CS$_2$ in the pygas from replacing at least a portion of the DMDS with H$_2$S is less in ethane steam cracking compared to propane steam cracking. Nevertheless, the modeling in Examples 3-7 compared to Comparative Examples 1 and 2 shows that replacement of DMDS with H$_2$S can have a significant effect on reducing the CS$_2$ concentration in the pygas, which will greatly improve the ability of olefin plants to manage the sulfur impurities level in the pygas and generate significant value.

Example 7

Figure 4:
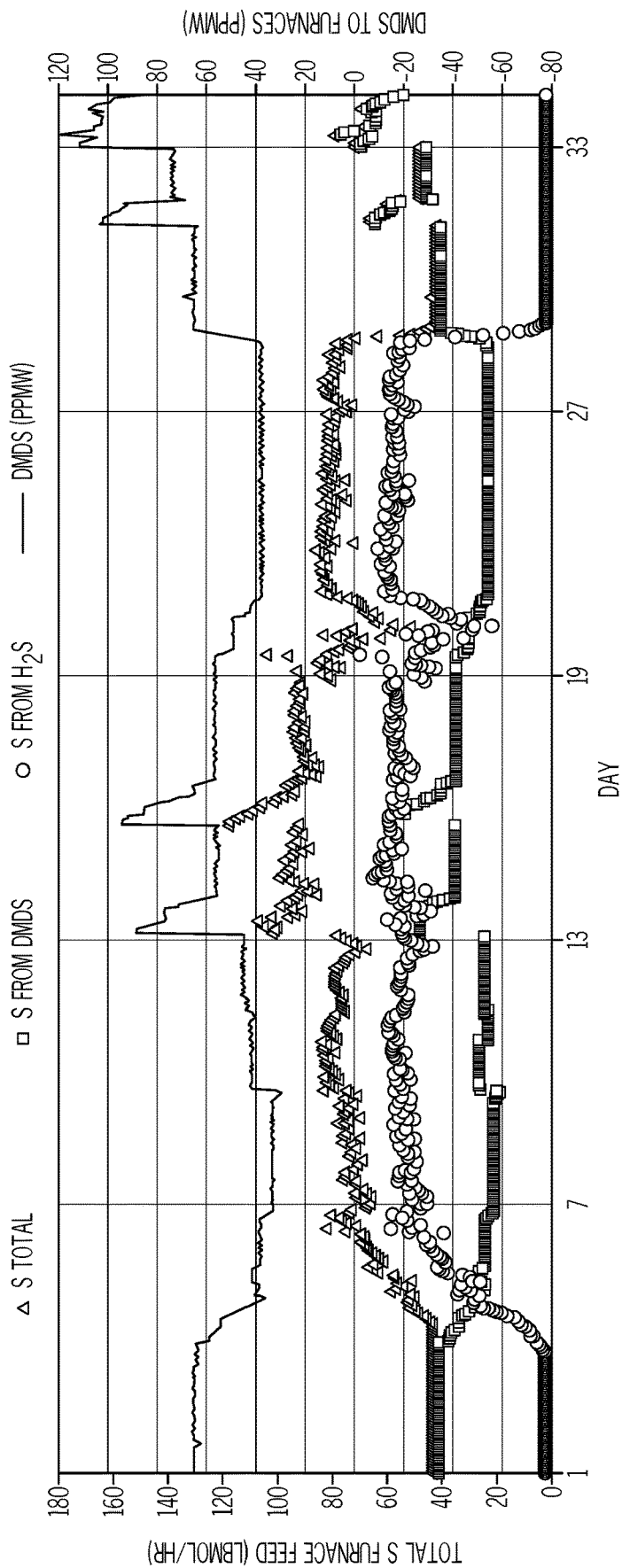
FIG. 4 graphically depicts a sulfur concentration (y-axis) in the steam cracking unit as a function of time (x-axis) for operation of the process with varying amounts of hydrogen sulfide introduced to the steam cracking unit, according to one or more embodiments described herein.

In Example 7, the effects of replacing increasing amounts of the DMDS with H$_2$S in an ethane steam cracking unit on the concentration of CS$_2$ in the pygas was investigated. In Example 7, a stream comprising ethane and H$_2$S were fed to the furnace of a 1500 kta ethylene production steam cracker. Referring to FIG. 4, the dosage of DMDS was adjusted to maintain a constant concentration of total elemental sulfur in the feed. The concentration of CS$_2$ in the pygas product was measured during the trial and the results are provided below in Table 2 along with the amounts of DMDS, H$_2$S, and concentration of total elemental sulfur.

TABLE 2

| Example | 7-1 | 7-2 | 7-3 | 7-4 |
| --- | --- | --- | --- | --- |
| DMDS feed | 65 | 38 | 33 | 38 |
| Total Elemental Sulfur (lbmol/h) | 43 | 70 | 74 | 78 |
| H$_2$S to furnaces (ppmv) | 1.8 | 45 | 54 | 55 |
| CS$_2$ in pygas (ppmv) | 9.3 | 4.9 | 5.2 | 3.9 |

Figure 5:
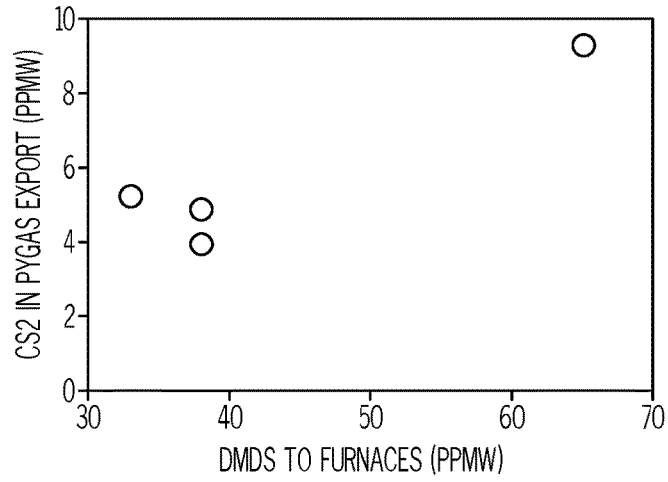
FIG. 5 graphically depicts a concentration of carbon disulfide in the pygas (y-axis) as a function of the concentration of DMDS introduced to the steam cracking unit (x-axis), according to one or more embodiments described herein.
Figure 6:
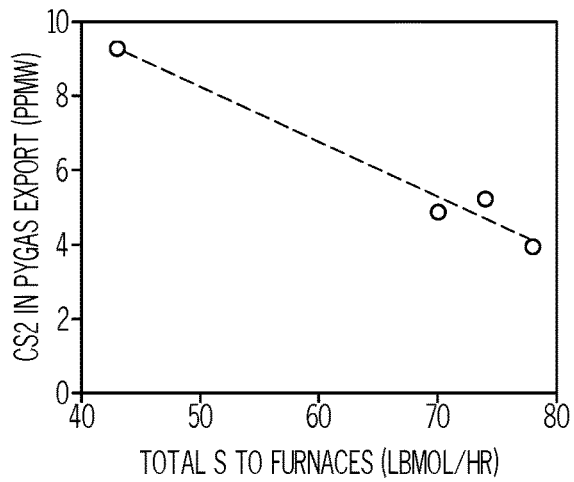
FIG. 6 graphically depicts a concentration of carbon disulfide in the pygas (y-axis) as a function of the total concentration of sulfur introduced to the steam cracking unit (x-axis), according to one or more embodiments described herein.
Figure 7:
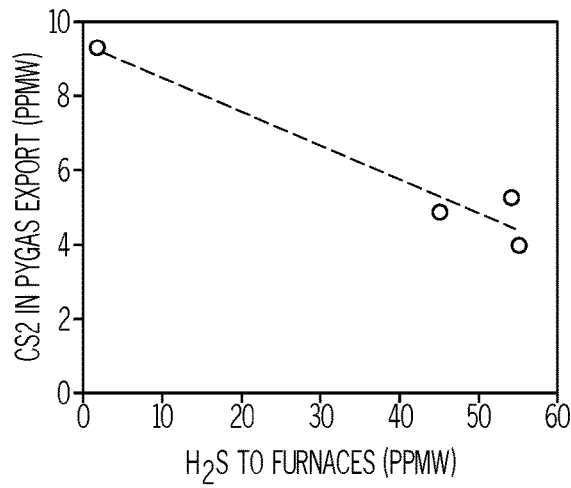
FIG. 7 graphically depicts a concentration of carbon disulfide in the pygas (y-axis) as a function of the concentration of hydrogen sulfide introduced to the steam cracking unit (x-axis), according to one or more embodiments described herein.

The concentration of CS2 in the pygas as a function of the amount of DMDS introduced to the furnace, the amount of total elemental sulfur introduced to the furnace, and the amount of H$_2$S introduced to the furnace are graphically depicted in FIGS. 4, 6, and 7, respectively. As shown by FIGS. 5-7, as the DMDS dosage was replaced by H$_2$S in the total sulfur feed, the concentration of CS$_2$ decreased significantly. No detrimental trends on the furnace coil differential pressures or the CO formation levels needed for the hydrogenation reactors were observed.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Generally, "inlet ports" and "outlet ports" of any system unit of the process 10 described herein refer to openings, holes, channels, apertures, gaps, or other like mechanical features in the system unit. For example, inlet ports allow for the entrance of materials to the particular system unit and outlet ports allow for the exit of materials from the particular system unit. Generally, an outlet port or inlet port will define the area of a system unit of the process 10 to which a pipe, conduit, tube, hose, material transport line, or like mechanical feature is attached, or to a portion of the system unit to which another system unit is directly attached. While inlet ports and outlet ports may sometimes be described herein functionally in operation, they may have similar or identical physical characteristics, and their respective functions in an operational system should not be construed as limiting on their physical structures.

It will be apparent to those skilled in the art that various modifications and variations can be made to the present invention without departing from the spirit and scope of the invention. Since modifications combinations, sub-combina-

The invention claimed is:

1. A method for producing olefins, the method comprising:
    passing a hydrocarbon feed comprising one or more hydrocarbons to a hydrocarbon cracking unit;
    passing a hydrogen sulfide containing stream to the hydrocarbon cracking unit, where:
        the hydrogen sulfide containing stream comprises hydrogen sulfide and a dilution gas;
        a concentration of hydrogen sulfide gas in the hydrogen sulfide containing stream is less than or equal to 10,000 ppmw; and
        a flow rate of the hydrogen sulfide containing stream to the hydrocarbon cracking unit is sufficient to produce a molar concentration of elemental sulfur in the hydrocarbon cracking unit of from 10 ppm to 200 ppm;
    cracking at least a portion of the hydrocarbon feed in the hydrocarbon cracking unit to produce a cracker effluent; and
    contacting the cracker effluent with a quench fluid in a quench unit to produce at least a cracked gas and a first pygas, wherein the cracked gas comprises at least one olefin product and the first pygas has a concentration of carbon disulfide less than 50 ppmw based on the total mass flow rate of the first pygas.

2. The method of claim 1, further comprising:
    passing at least a portion of the cracked gas to a cracked gas separation system that separates the cracked gas into at least a hydrogenation feed comprising acetylene, carbon monoxide, hydrogen, and the at least one olefin product and a cracked gas bottom stream comprising at least pyrolysis gasoline components; and
    passing the cracked gas bottom stream to a cracked gas bottoms separation system that separates the cracked gas bottom stream into a second pygas and at least one light boiling stream;
    wherein the second pygas has a concentration of carbon disulfide less than 50 ppmw based on the total mass flow rate of the second pygas.

3. The method of claim 1, further comprising:
    passing the cracked gas to an acetylene hydrogenation unit as a hydrogenation feed to the acetylene hydrogenation unit;
    contacting the cracked gas with an acetylene hydrogenation catalyst in an acetylene hydrogenation unit, the contacting causing hydrogenation of at least a portion of the acetylene in the cracked gas to produce a hydrogenation effluent; and
    passing the hydrogenation effluent to a hydrogenation effluent separation system that separates the hydrogenation effluent into a third pygas and at least one product stream comprising ethylene, propylene, butenes, or combinations of these;
    wherein the third pygas has a concentration of carbon disulfide less than 50 ppmw based on the total mass flow rate of the second pygas.

4. The method of claim 1, wherein passing the hydrogen sulfide containing stream to the hydrocarbon cracking unit comprises passing the hydrogen sulfide containing stream directly to the hydrocarbon cracking unit or combining the hydrogen sulfide containing stream with the hydrocarbon feed upstream of the hydrocarbon cracking unit.

5. The method of claim 4, wherein the dilution gas comprises one or more of ethane, propane, butanes, or combinations of these.

6. The method of claim 4, further comprising recycling at least a portion of ethane, propane, butanes, or combinations of these, recovered from the cracked gas as at least a portion of the dilution gas of the hydrogen sulfide containing stream.

7. The method of claim 4, wherein the hydrogen sulfide containing stream does not include compounds comprising both carbon and sulfur in the same molecule.

8. The method of claim 4, wherein the hydrogen sulfide containing stream does not include dimethyl disulfide, dimethyl sulfide, diethyl sulfide, methyl mercaptan, or combinations of these.

9. The method of claim 4, further comprising:
    passing an organosulfur compound stream and hydrogen to a catalytic decomposition unit upstream of the hydrocarbon cracking unit;
    contacting the organosulfur compound stream and hydrogen in the presence of a catalyst in the catalytic decomposition unit at a reaction temperature less than 350° C., where the contacting causes at least a portion of organosulfur compounds from the organosulfur compound stream to react to produce a catalytic decomposition effluent comprising hydrogen sulfide gas; and
    passing the catalytic decomposition effluent to the hydrocarbon cracking unit as at least a portion of the hydrogen sulfide containing stream.

10. The method of claim 4, further comprising increasing or decreasing a concentration of hydrogen sulfide gas in the hydrogen sulfide containing stream or a flow rate of the hydrogen sulfide containing stream to increase or decrease the concentration of elemental sulfur in the hydrocarbon cracking unit.

11. The method of claim 4, further comprising increasing or decreasing a concentration of hydrogen sulfide gas in the hydrogen sulfide containing stream, a flow rate of the hydrogen sulfide containing stream, or both, to adjust a concentration of carbon monoxide in the cracked gas.

12. The method of claim 1, wherein the hydrogen sulfide passivates internal furnace coils in the hydrocarbon cracking unit to reduce coke formation.

13. The method of claim 1, further comprising introducing dimethyl disulfide, dimethyl sulfide, diethyl sulfide, methyl mercaptan, or combinations of these to the hydrocarbon cracking unit separate from the hydrogen sulfide containing stream.

14. The method of claim 1, wherein an amount of elemental sulfur contributed by the hydrogen sulfide gas introduced to the hydrocarbon cracking unit as a percentage of the total elemental sulfur in the hydrocarbon cracking unit is greater than zero percent and less than or equal to 100%.

* * * * *